(12) United States Patent
Kissel et al.

(10) Patent No.: US 6,616,944 B2
(45) Date of Patent: Sep. 9, 2003

(54) SELF-ASSEMBLING COLLOIDAL CARRIERS FOR PROTEIN DELIVERY

(75) Inventors: Thomas Kissel, Staufen (DE); Armin Breitenbach, Monheim (DE); Tobias Jung, Aachen (DE); Walter Kamm, Hofheim (DE)

(73) Assignee: Medinnova Gesellschaft fur Medizinsche Innovationen aus Adkademischer Forschung mbH, Marburg (DE)

( * ) Notice: Subject to any disclaimer, the term of this patent is extended or adjusted under 35 U.S.C. 154(b) by 0 days.

(21) Appl. No.: 09/801,189

(22) Filed: Mar. 8, 2001

(65) Prior Publication Data

US 2001/0047074 A1 Nov. 29, 2001

Related U.S. Application Data

(60) Provisional application No. 60/187,869, filed on Mar. 8, 2000.

(51) Int. Cl.$^7$ ................................................. A61K 9/38
(52) U.S. Cl. ..................... 424/477; 528/354; 528/361; 528/364; 525/56; 525/58; 525/63; 525/88; 525/89; 525/437; 525/440; 424/409; 424/457; 424/484; 424/491; 424/499; 424/427; 424/434; 424/435; 514/2; 514/4; 524/801; 524/803
(58) Field of Search ..................... 528/354, 361, 528/364; 525/437, 440, 56, 58, 63, 88, 89; 424/409, 457, 477, 484, 491, 499, 427, 434, 435; 514/2, 4; 524/801, 803

(56) References Cited

U.S. PATENT DOCUMENTS 5,919,442 A  *  7/1999  Yin et al. ................ 424/78.18
5,929,196 A  *  7/1999  Kissel et al. ................ 528/271

FOREIGN PATENT DOCUMENTS

| DE | 198 39 515 | * | 3/2000 |
| GB | 2 145 422 | * | 3/1985 |
| WO | 99/52560 | * | 10/1999 |

OTHER PUBLICATIONS

Breitenbach, et al., Biodegradable comb polyesters: Part 1 Synthesis, characterization and structural analysis of poly-(lactide) and poly(lactide–co–glycolide) grafted onto water–soluble poly(vinyl alcohol) as backbone, Polymer, GB, Elsevier Science Publishers B.V, vol. 39, NR. 14, pp. 3261–3271.*

* cited by examiner

Primary Examiner—Samuel A. Acquah
(74) Attorney, Agent, or Firm—Foley & Lardner

(57) ABSTRACT

The invention is directed to self-assembling, polymer-based delivery systems for proteins. The delivery systems comprises an active agent and a polyol ester of the invention, having a linear polyol containing six or more hydroxyl groups as a central backbone and biodegradable hydroxy carboxylic ester groups attached to the central backbone.

32 Claims, 19 Drawing Sheets

ESTIMATED RESPONSE SURFACE

ESTIMATED RESPONSE SURFACE

STANDARDIZED PARETO CHART

FIG. 18

IgA TITERS AFTER ORAL ADMINISTRATION OF DIFFERENT TETANUS TOXOID FORMULATIONS

FIG. 19

IgG TITERS AFTER ORAL ADMINISTRATION OF DIFFERENT TETANUS TOXOID FORMULATIONS

SELF-ASSEMBLING COLLOIDAL CARRIERS FOR PROTEIN DELIVERY

This application claims the benefit of Provisional Application No. 60/187,869, filed Mar. 8, 2000.

FIELD OF THE INVENTION

The present invention is directed to a self-assembling, polymer-based drug delivery system constructed from water-soluble polyesters. The delivery system forms stable complexes with proteins and is useful as a drug carrier for therapeutic use or vaccines.

BACKGROUND OF THE INVENTION

Recombinant DNA technology has provided a wide variety of proteins, peptides, and oligonucleotides which may be of considerable therapeutic value. V. H. Lee, "Changing Needs in Drug Delivery in the Era of Peptide and Protein Drugs, in V. H. Lee eds, *Peptide and Protein Drug Delivery*, 1–56 (Marcel Decker, New York, 1991); and J. E Talmadse, "The Pharmaceutics and Delivery of Therapeutic Polypeptides and Proteins," *Adv. Drug Deliv. Rev.*, 10:247–299 (1993). Parenteral delivery of such hydrophilic macromolecules as drugs necessitates polymeric delivery systems, such as microspheres, implants, and nanospheres. R. Langer, "New Methods of Drug Delivery," *Science*, 249:1527–1533 (1990). Drug release rates and biodegradation need to be carefully controlled to provide save and efficacious devices for chronic therapy.

The protection of biologically active proteins against denaturation and enzymatic degradation is an important issue for all drug delivery systems. Possible strategies based on polymeric carriers for oral and parenteral delivery of proteins include: (a) modification of biologically active compounds with polymers, (b) encapsulation of the hydrophilic macromolecules into micro- or nanospheres, and (c) adsorptive drug loading onto the surface of nanospheres. Allemann et al., "Drug-Loaded Nanoparticles; Preparation Methods and Drug Targeting Issues," *Eur. J. Pharm. Biopharm.*, 39:173–191 (1993).

Covalent modification of proteins with polymers, e.g. by 'pegylation', can be used for altering and controlling a drug's pharmacokinetics, biodistribution, and often toxicity. Monfardini et al., "Stabilization of Substances in Circulation," *Bioconjugate Chem.*, 9:418–450 (1998). Anionic polymer-drug conjugates, parenterally applied, have shown persistently higher plasma levels, even gradually accumulating in peripheral tumors. In contrast, cationic drug conjugates are trapped by the liver and blood vessels and rapidly cleared from circulation. Takakura et al., "Development of a Novel Polymeric Prodrug of Mitomycin C, Mitomycin C-dextran Conjugate with Anionic Charge; I. Physicochemical Characteristics and In Vivo and In Vitro Antitumor Activities," *Int. J. Pharm.*, 37135–143 (1997). There are two limitations of the polymer conjugation strategy; first, the protein must contain suitable functional groups for derivatization; and second, modification of those groups may lead to a decrease or even loss of biological activity.

Several problems associated with micro- and nanoencapsulation of proteins are associated with general preparation parameters, e.g. the use of toxic emulgators in emulsion or dispersion polymerization (Kreuter J., "Evaluation of Nanoparticles as Drug-delivery Systems; Preparation Methods," *Pharm. Acta Helv.*, 58:196 (1983)) or the application of high shear forces during emulsification processes (Quintanar-Guerrero et al., "Preparation Techniques and Mechanisms of Formation of Biodegradable Nanoparticles from Preformed Polymers," *Drug Dev. Ind. Pharm.*, 24:11138 (1998)). In addition, polymeric issues, such as insufficient biocompatibility and biodegradability, balance of hydrophilic and hydrophobic moieties, etc., can lead to insufficient drug release.

Especially in oral drug delivery, very small lipophilic poly(styrene) nanospheres (NP) seem to allow mucosal particle absorption. Jani et al., "Nanoparticle Uptake by the Rat Gastrointestinal Mucosa: Quantitation and Particle Size Dependency," *J. Pharm. Pharmacol.*, 42:821–826 (1990). It was reported that negatively charged NP prepared from sebacid and fumaric acid copolymers (Mathiowitz et al., *Nature*, 386:410–414 (1997) as well as anionic liposomes showed substantial intestinal uptake. A promising strategy might be the use of polymeric carriers combining all properties described above, namely biodegradability and the possibility to engineer the NP surface by manipulation of the balance of hydrophilic and hydrophobic domains as well as surface charges. The ideal technological method would manage without emulsion or shear forces and, therefore, would be based on self-assembly. Such macromolecular self-assembling systems have attracted increasing attention as carriers for drug delivery. "Biologically Erodable Microspheres as Potential Oral Drug Delivery Systems," *Nature*, 386:410–414 (1997); Tomizawa et al., "Uptake of Phosphatidylserine Liposomes by Rat Peyer's Patches Following Intraluminal Administration," *Pharm. Res.*, 10:549–552 (1993); Dumitriu et al., "Inclusion and Release of Proteins from Polysaccharide-based Polyion Complexes," *Adv. Drug Deliv. Rev.*, 31223–2465 (1998); and Jeong et al., "Drug Release from Biodegradable Injectable Thermosensitive Hydrogel of PEG-PLGA-PEG Triblock Copolymers," *J. Controlled Release*, 63(1–2):155–63 (2000).

The versatility of nanoparticles prepared by controlled precipitation from biodegradable amphiphilic charge modified comb polyesters as a colloidal protein delivery system has recently been demonstrated. Breitenbach et al., *Pharm. Sci. Suppl.*, 1(1):300 (1998); Jung et al., *Pharm. Sci. Suppl.*, 1(1):299 (1998); and Kamm et al., *Pharm. Sci. Suppl.*, 1(1):299 (1998).

In addition, recently nanospheres with designed surface structure prepared from biodegradable comb polyesters for oral and nasal vaccination have been described. The nanospheres consist of poly(lactide-co-glycolide) brush-like grafted onto charged or uncharged poly(vinyl alcohol) backbones. Nguyen et al., "Evaluation of Polyetherpolyethyleneimine Graft Copolymers as Gene Transfer Agents," Gene Ther., 7(2):126–38 (2000); and Fischer et al., "A Novel Non-viral Vector for DNA Delivery Based on Low Molecular Weight, Branched Polyethylenimine: Effect of Molecular Weight on Transfection Efficiency and Cytotoxicity," *Pharm. Res.*, 16(8):1273–9 (1999).

There remains a need in the art for drug delivery methods for peptides and proteins. The present invention satisfies this need.

SUMMARY OF THE INVENTION

The present invention is directed to water-soluble comb polyesters and their use as particulate protein delivery systems. The compositions exhibit temperature dependent self-assembly properties. The compositions are superior to prior art methods as their preparation does not require the use of solvents or surfactants.

The polyol esters of the invention preferably comprise: (a) a linear polyol containing six or more hydroxyl groups as a central backbone; and (b) biodegradable hydroxy carboxylic ester groups attached to the central backbone, wherein the linear polyol contains charged groups, proton donating groups, and/or proton accepting groups, which are attached via a spacer group or an ether-, ester-, or urethane-linkage to the linear polyol.

One aspect of the invention is directed to particulate forms of the water-soluble comb polyesters of the invention, either alone or in combination with one or more water-soluble active agents, such as peptides or proteins. In addition, the polyesters of the invention can be in the form of a complex, either alone or in combination with one or more water-soluble active agents, such as a peptide or protein. Preferably the particulate forms of the polyesters of the invention, either alone or in combination with an active agent, have a mean diameter particle size of less than about 10 microns.

Yet another aspect of the invention is directed to pharmaceutical compositions comprising the particulate water-soluble comb polyesters of the invention.

The invention also comprises methods of treating organisms in need, including mammals such as humans, with a composition of the invention. Methods of administration include, but are not limited to, oral, nasal, and pulmonary routes of administration.

The invention encompasses methods of making a complex comprising a polyester of the invention. Such methods comprise, for example, providing an aqueous solution of a polyol ester of the invention and increasing the temperature until a spontaneous in-situ formation of particles of polyol ester occurs. In this method, the aqueous solution of polyol ester can additionally comprise an active ingredient. In this version of the method, particles of polyol ester/active ingredient complex are formed following an increase in temperature.

Yet another method of making a complex comprising a polyester of the invention comprises providing an aqueous solution of a polyol ester of the invention, followed by adding a drug molecule having substituents which are capable of forming complexes with one or more of the ionic groups, proton accepting groups, and/or proton donating groups of the polyol ester to form particles of a polyol ester/drug molecule complex. Such substituents can be, for example, ionic groups, proton accepting groups, and proton donating groups. After formation of the polyol ester/drug molecule complex particles, additional drug molecules can be added to the composition. Such additional drug molecules are adsorbed by non-ionic interaction by the complex particles.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 18: Shows IgA titers after oral adminstration of different tetanus toxoid formulations; and FIG. 19: Shows IgG titers after oral adminstration of different tetanus toxoid formulations.

DETAILED DESCRIPTION OF THE PREFERRED EMBODIMENTS

Figure 1:
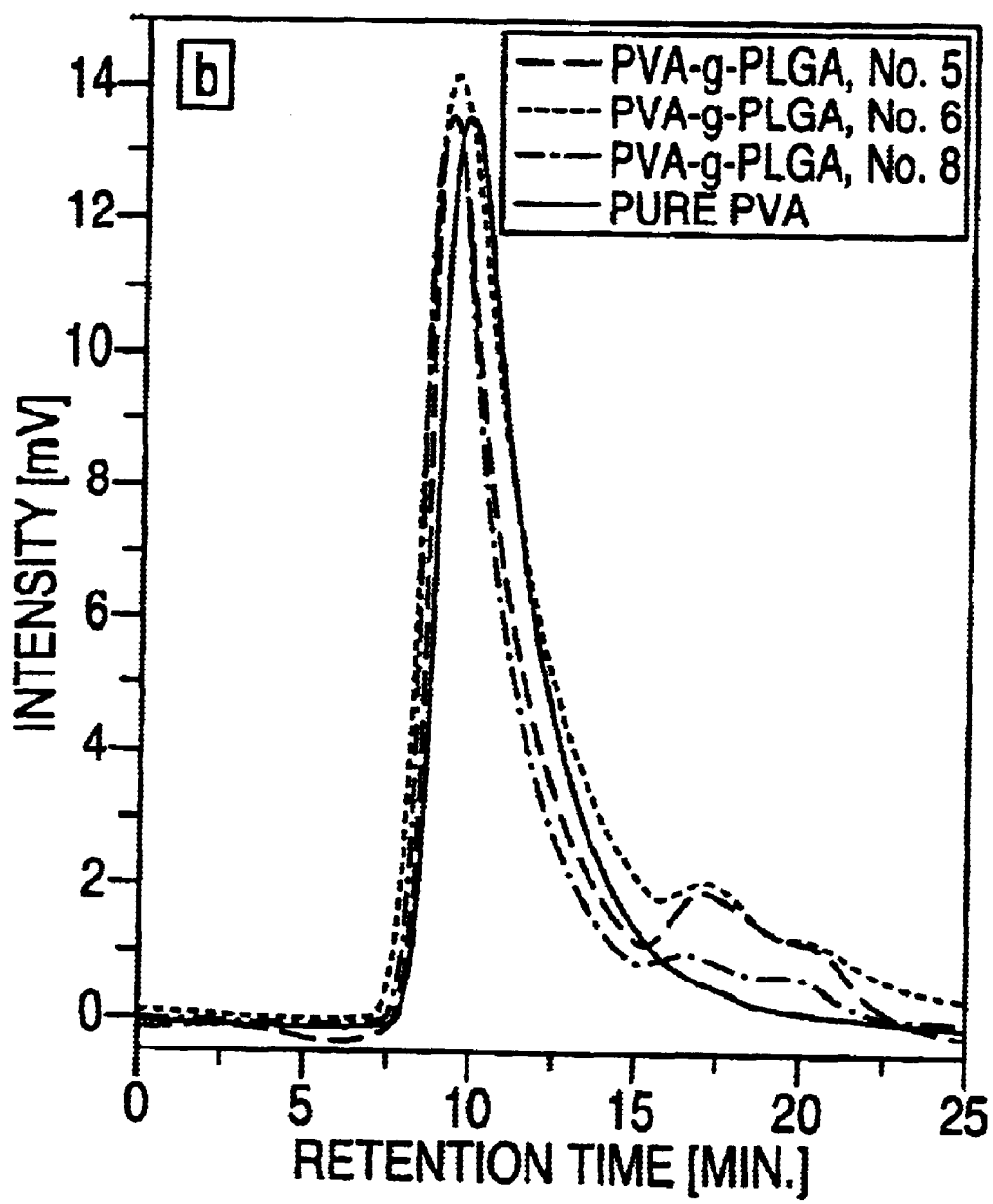
FIG. 1: Shows a SEC analysis of bulk polymers.

Structure modified PLGA have been investigated for several years, since these polymers offer additional options to manipulate their balance of hydrophobic and hydrophilic domains. Nguyen et al., *Gene Ther.*, 7(2):126–38 (2000); Fischer et al., "A Novel Non-viral Vector for DNA Delivery Based on Low Molecular Weight, Branched Polyethylenimine: Effect of Molecular Weight on Transfection Efficiency and Cytotoxicity," *Pharm. Res.*, 16(8):1273–9 (1999); Breitenbach et al., "Biodegradable Comb Polyesters by Brush-like Grafting PLGA onto Polyelectrolyte Backbones: A Feasible Carrier for the Preparation of Nanoparticles with Defined Surface Structure," Breitenbach et al., *Macromolecular Symposia* (Springer Verlag 2001); Jung et al., "Oral and Nasal Administration of Tetanus Toxoid Loaded Nanoparticles Consisting of Novel Charged Biodegradable Polyesters for Mucosal Vaccination," *Proc. Int. Symp. Control. Rel. Bioact. Mater.*, 26:5021 (1999); Breitenbach et al., "Self-Assembling Colloidal Carriers for Protein Delivery: Nanoparticulate Polymer Protein Conjugates with Novel Watersoluble Biodegradable Comb Polyolesters," *Proc. Int. Symp. Control. Rel. Bioact. Mater.*, 26:248 (1999); Kissel et al., "Biodegradable Nanoparticles for Oral Delivery of Peptides: Is There a Role for Polymers to Affect Mucosal Uptake?," *Eur. J. Pharm. Biopharm.*, 50(1):147–160 (2000); Breitenbach et al., *Polymer*, 39(14):3261–3271 (1998); and Breitenbach et al., "Branched Biodegradable Polyesters for Parenteral Drug Delivery Systems," *J. Controlled Release*, 64(1–3):167–78 (2000).

For example, variation of the PLGA side chain lengths grafted onto the backbone polyols allows adjustment of properties, such as molecular weight (Mw), degree of crystallinity, glass transition temperature (Tg), and solubility.

The novel biodegradable polyesters, consisting of short poly(lactone) chains grafted onto poly(vinyl alcohol) (PVA) or charge modified sulfobutyl-PVA (SBPVA), were prepared by bulk melt polymerization of lactide and glycolide in the presence of the different core polyols. The modified backbones were obtained by reacting activated PVA with sulfobutyl groups.

Specifically, a self-assembling, polymer-based delivery system for proteins was obtained from water-soluble comb polyesters and a number of model proteins. The polyesters were prepared by bulk melt grafting of poly(lactic-co-glycolic acid) (PLGA) chains onto poly(vinyl alcohol) (PVA) or negatively charged poly(2-sulfobutyl-vinyl alcohol) (P(SB-VA)). Adjustment of the PLGA chain lengths by feed composition allowed modification of polymer properties, such as molecular weight and solubility. While polyesters with an average of 5 PLGA units per chain showed good acetone solubility, further chain length reduction yielded water-soluble polymers.

In aqueous solution, a lower critical solution temperature was observed for these polyesters, which also could be manipulated by PLGA chain lengths. The polymers showed stimuli-sensitive properties enabling the formulation of protein drug delivery systems either by temperature trigger or by ionic interaction.

Polyol Esters of the Invention

The polyol esters of the invention preferably comprise (a) a linear polyol containing six or more hydroxyl groups as a central backbone; and (b) biodegradable hydroxy carboxylic ester groups attached to the central backbone, wherein the linear polyol contains charged groups, proton donating groups, and/or proton accepting groups which are attached via a spacer group or an ether-, ester-, or urethane-linkage to the linear polyol. The spacer group can be an aliphatic group.

The polyol backbone can be, for example, linear synthetic polymers having greater than about 6 and less than or equal to about 500 hydroxyl groups; polyvinyl alcohols having polymerization degrees of more than 6 and up to 500; or a linear synthetic vinylcopolymer. Such a linear synthetic vinylcopolymer can be a polyvinyl alcohol having polymerization degrees of more than about 6 and up to about 500.

Preferred backbones include vinylpyrrolidones, vinylamines, vinylimidazoles, vinylpyridines, vinyl sulfonic acids, and vinyl phosphonic acids.

The charged groups, proton donating groups, and/or proton accepting groups of the polyol ester, attached via a spacer group to the backbone, can be carboxylic acid groups, sulfonic acid groups, sulfate groups, primary quaternary amino groups, secondary quaternary amino groups, tertiary quaternary amino groups, and/or quaternary amino groups.

The biodegradable hydroxy carboxylic acid groups can be derived from one or more of l-lactic acid, d-lactic acid, ε-caprolactone, and/or glycolic acid. The biodegradable hydroxy carboxylic acid groups can also be derived from dimers of one or more of l-lactic acid; d-lactic acid; d,l-lactic acid; and glycolic acid in any molar composition. In one embodiment of the invention, introduction of the biodegradable hydroxy carboxylic acid groups into the molecule retains the water-solubility of the central backbone.

The hydroxy carboxylic add groups connected to the central backbone preferably comprise about 1 to about 100 hydroxy carboxylic acid units, or about 5 to about 50 hydroxy carboxylic acid units.

The molar proportion of polyol hydroxyl groups and hydroxy carboxylic acid units in the polyol ester can be in the range of between about 0.6:1 and about 6:1, or between about 1:1 and about 3:1.

In one embodiment of the invention, the groups connected via a spacer group to the backbone contain one or more substituents, such as carboxylic groups, sulfobutyl groups, and sulfopropyl groups. Such groups can also be butylamino-, propylamino- and ethylamino groups as primary, secondary, tertiary, or quaternary amino groups, wherein N-substituents can contain hydrogen or alkyl groups. In this embodiment, the alkyl groups are preferably methyl and/or ethyl groups.

The polyol esters of the invention can be characterized by a lower critical solution temperature (LCST) in aqueous solution in the temperature range between about 0 and about 100° C.

Complexes of the Invention

The invention also comprises particulate complexes comprising a polyol ester according to claim 1 and an active ingredient. Such an active ingredient is preferably a water-soluble molecule possessing pharmacological activity, such as a peptide, protein, enzyme, enzyme inhibitor, antigen, cytostatic agent, antiinflammatory agent, antibiotic, DNA-construct, RNA-construct, or growth factor. The complexes of the invention preferably have a mean particle diameter of less than about 10 $\mu$m, or less than about 1 $\mu$m.

Methods of Treatment

The invention encompasses methods of administering the complexes and polymers of the invention to an organism in need, such as a human. Administration can be via any conventionally known method. When adapted for mucosal vaccination, the active ingredient is preferably a peptide, protein, RNA, or DNA. Other useful routes of administration of the complexes of the invention include, but are not limited to, pulmonary and nasal routes of administration.

Methods of Making the Complexes of the Invention

The invention also encompasses methods of making a complex comprising a polyester of the invention. Such methods comprise, for example, providing an aqueous solution of a polyol ester of the invention, and increasing the temperature of the solution until a spontaneous in-situ formation of particles of polyol ester occurs. In this method, the aqueous solution of polyol ester can additionally comprise an active ingredient. In this version of the method, particles of polyol ester/active ingredient complex are formed following an increase in temperature.

The temperature of the polyester, or polyester/active agent, solution can be increased above a lower critical solution temperature (LCST), which is in the range of between about 0 and about 100° C.

Yet another method of making a complex comprising a polyester of the invention comprises providing an aqueous solution of a polyol ester of the invention, followed by adding a drug molecule having substituents which are capable of forming complexes with one or more of the ionic groups, proton accepting groups, and/or proton donating groups of the polyol ester to form particles of a polyol ester/drug molecule complex. Such substituents can be, for example, ionic groups, proton accepting groups, and proton donating groups. After formation of the polyol ester/drug molecule complex particles, additional drug molecules can be added to the composition. Such additional drug molecules are adsorbed by non-ionic interaction by the complex particles.

Characterization of the Polymers and Complexes of the Invention

Spontaneous reversible formation of complexes with a number of relevant proteins was observed. In the case of polyelectrolyte complexes with charged polymers, a suitable candidate could be any protein if processed at a pH below its point of isocharge. Especially basic proteins, such as e.g. cytochrome C, enable polyelectrolyte complexation at pH values near physiological conditions. Experimental data confirm that under these conditions an unwanted reaction with plasma proteins such as albumin is unlikely to occur.

The best solvent for polymers with a PLGA chain lengths in the range of about 10 to 30 repeating units was found to be dichloromethane. A reduction to on average of 5 to 10 units increased polymer amphiphilicity and resulted in acetone solubility. Polymers with even shorter PLGA chains become water-soluble.

The polymers were characterized by methods such as NMR and IR spectroscopy as well as combined GPC and static laser light scattering. Lower critical solution temperatures (LCST) were investigated by turbidimetry measurements.

Spontaneous formation of colloidal polymer-protein conjugates with a variety of proteins was observed. Spontaneous self-assembled polymer-protein conjugates, with proteins such as bovine and human serum albumin, tetanus toxoid, and cyctochrom C, were characterized by dynamic laser light scattering, UV-VIS spectroscopy, SEM, EDX, TEM, and PAGE, as described in the examples below.

Complex mean diameter particle sizes ranging from about 100 nm to several microns, and 'drug loadings' of up to 200% (w/w), could be systematically manipulated by factors such as pH, temperature, and type of polymer. Complex formation was fully reversible, thus enabling the preparation of drug release systems. While colloid sizes were controllable by adjustment of concentrations, solution pH, and ionic strengths, the release rates of the complexed proteins could be equally manipulated by pH value. Increased bioadhesion and initial oral vaccination data in mice indicate the considerable potential of this system in controlled drug delivery.

The successful synthesis of novel comb polyesters could be demonstrated most clearly by NMR and IR spectroscopy as well as static light scattering analysis (see e.g., Table 1, below).

TABLE 1

| Polymer | PVA:(LA:GA) [mol:(mol + mol)] | Molecular Weight Mw (SLS) [kg/mol] |
|---|---|---|
| PVA | — | 24.085 |
| PVAPLG62.5 | 1.38:(0.53 + 0.47) | 56.290 |
| PVAPLG57.1 | 1.11:(0.53 + 0.47) | 70.230 |
| PVAPLG50 | 0.83:(0.53 + 0.47) | 76.390 |
| SB10PVAPLG50* | 0.83:(0.53 + 0.47) | n.d. |

*10% of PVA-OH etherified with sulfobutyl groups

By careful adjustment of polylactone chain lengths, it was possible to custom tailor polymer properties, such as molecular weight and solubility, over a broad range.

The shorter the more lipophilic polyester chains, the more marked the amphiphilic character of the resulting comb polymers, leading to a novel class of water-soluble PLGAs.

Moreover, in aqueous solution the polymers showed a distinct lower critical solution temperature (LSCT) as a function of polymer composition. The shorter the ester chains, the lower the observed LCSTs.

Addition of a protein solution to the aqueous polymer solutions described in the examples led to spontaneous formation of colloidal polymer-protein conjugates with a wide variety of proteins. Sizes of the colloidal complexes, ranging from below 100 nm to several microns, and drug loadings of up to 100%, could be systematically manipulated by factors such as pH, temperature, and type of polymer.

While for the use of uncharged polymers hydrophilic-hydrophobic interactions are proposed, charged groups in the polymer backbone led to ionic interactions with the investigated proteins.

A conjugate of the polyester PVAPLG57.1 and cytochrom C, provides a typical example of the conjugate morphology.

Results on increased bioadhesion in Caco-2 cell cultures, as well as successful oral in vivo vaccination in mice using tetanus toxoid-polymer conjugates, suggests that these polymers are useful for colloidal protein delivery.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to demonstrate polymer syntheses and to characterize resultant polymers.

Materials: Poly(vinyl alcohol) (PVA, Mw: 15'000 g/mol, degree of hydrolysis: 88%) was obtained from Fluka, rigorously dried at 80° C. in vacuo until a constant weight was obtained, and stored in a desiccator under vacuum at room temperature over $P_2O_5$. D,L-lactide and glycolide (Boehringer Ingelheim, S-grade) were recrystallized twice from dry ethyl acetate (refluxed over calcium hydride) and dried for 48 hours in vacuo directly before use. The melting points were 125–126° C. and 82–83° C., respectively. Stannous octoate (Aldrich), 1,4-butanesultone (purum, Fluka), and all other materials were of analytical grade and used as received. Sodium hydride (Merck-Schuchard) was purified by extraction three times with pentane. DMSO (99.5%, Riedel-de Haën) was dried over calcium hydride (Riedel-de Haën) and distilled under reduced pressure directly before use. Fluorescently labeled bovine serum albumin (FITC-BSA) and cytochrom C (CytC) were purchased from Sigma, tetanus toxoid (Ttx) and human serum albumin (HSA) were kindly provided from Chiron-Behring. Dextran sulfate sodium (DSS) and diethyaminoethyidextran (DEAED) were purchased from Sigma.

Polyelectrolyte Backbones. Poly(2-sulfobutyl-vinyl alcohol), P(SB-VA), was prepared from PVA under anhydrous conditions in a dry nitrogen atmosphere. Nguyen et al., *Gene Ther.*, 7(2):126–38 (2000); and Breitenbach et al., *Macromolecular Symposia* (Springer Verlag 2001). PVA was activated with the carbanion of DMSO, obtained by its reaction with sodium hydride, and etherified with 1,4-butanesultone at room temperature.

Ultrafiltration was performed four times on each sample (initial concentration: 200 mg polymer in 10 ml water) with an Amicon ultrafiltration stirring cell 8010 equipped with a YM1 filter membrane (Amicon, cut off=1000 g/mol).

Sulfur Analysis of ultrafiltrated P(SB-VA)s was performed by Schoeniger method.

Polyesters. Biodegradable comb polyesters were prepared by bulk melt grafting poly(lactic-co-glycolic acid) onto the different polyols (PVA, P(SB-VA)). Nguyen et al., *Gene Ther.*, 7(2):126–38 (2000); and Breitenbach et al., *Macromolecular Symposia* (Springer Verlag 2001). In brief, ring-opening polymerization of the lactones, L-lactide or D,L-lactide and glycolide, in the presence of the different core PVAs with stannous octoate as catalyst was used.

The hydroxyl groups of the polymers effectively initiate this type of ring opening polymerization, as reported recently. Breitenbach et al., *Proc. Int. Symp. Control. Rel. Bioact. Mater.*, 26:248 (1999). The backbone polyols used were (1) an unmodified 15'000 g/mol poly(vinyl alcohol) (PVA) and (2) PVAs bearing negative charges. The charged groups were introduced by coupling 15'000 g/mol PVA with 1,4-butanesultone. Nguyen et al., *Gene Ther.*, 7(2):126–38 (2000); and Breitenbach et al., *Macromolecular Symposia* (Springer Verlag 2001).

Reaction time was 10 minutes at 170° C. to achieve sufficient solubility of the polyols in the melt of the lactones. The reaction was then allowed to continue for an additional 3 hours at 150° C. Purification of the water-soluble polyesters was performed by ultrafiltration.

The polymers obtained, shown in Table 2 are characterized by a three-dimensional comb architecture.

aqueous SEC analysis, a column combination Suprema $10\mu$ and Suprema linear $10\mu$–$8\times300$ mm [PSS] was applied.

Figure 2:
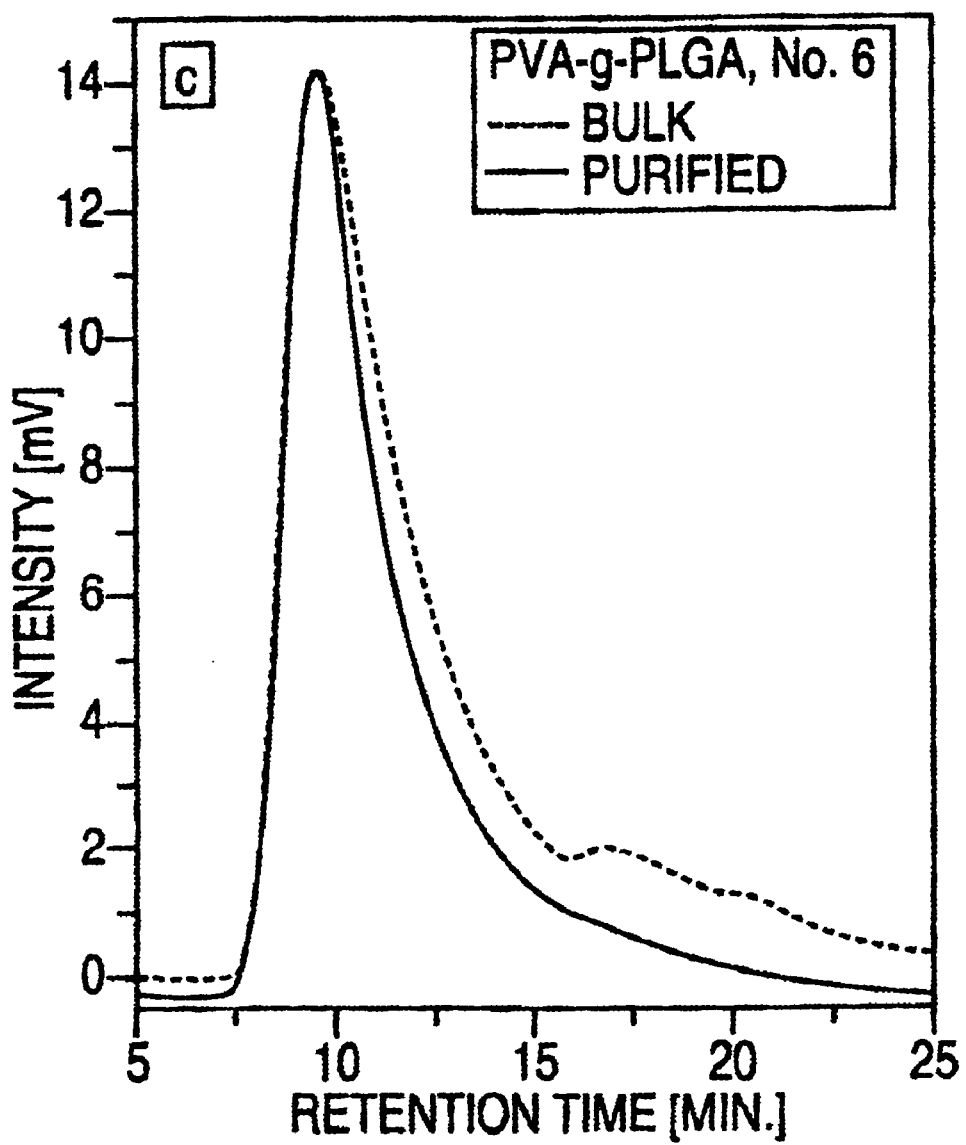
FIG. 2: Shows a SEC analysis of bulk polymers following ultrafiltration.

The influence of the grafting reaction on polymer molecular weights can be seen in their SEC traces, indicating that the water-soluble polymers all exhibited comparable Mw. Since reaction temperatures were relatively high (170° C./150° C.), a small amount of by-products and/or monomers was visible at retention times of about 16 to 22 minutes. Their successful removal by ultrafiltration of the aqueous polymer solutions through a 1000 g/mol cut-off membrane is demonstrated in FIG. 2.

Figure 3:
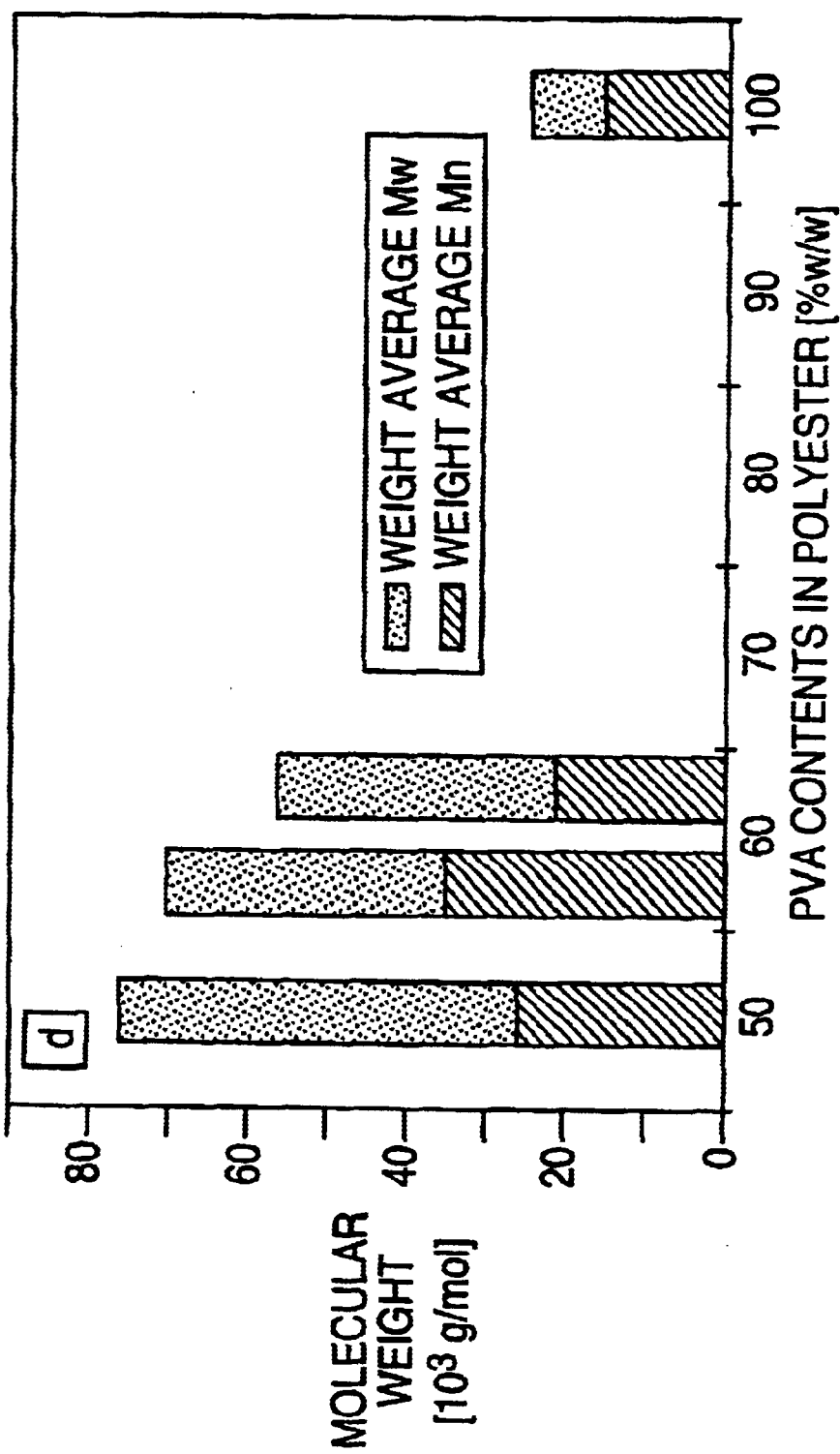
FIG. 3: Shows absolute Mw as a function of polymer composition.

SEC analysis is not the method of choice to determine molecular weights of comb polymers, since it underestimates the Mw due to smaller polymer hydrodynamic volume in solution compared to linear reference material. Neither application of 3rd order calibration with pullulan nor PVA standards yielded reasonable values. Therefore, some selected polymers were analyzed by a combination of SEC and Static Light Scattering (SLS) to characterize their effective molecular weights. The values ranging from several hundred thousand g/mol to significantly below are listed in Table 3, below, confirming, that the Mw directly followed synthesis feeds, as outlined in FIG. 3, the more polyol present, the lower the polymer Mw.

It was not possible to find a suitable column/eluent combination for SEC-SLS analysis of the charged polymers, which strongly interacted with the SEC columns. Therefore, intrinsic viscosities determined from aqueous 0.5M $NaNO_3$ solutions were used as a qualitative measure, indicating that the negative polymers used in this study exhibited molecular weights quite comparable to the uncharged polymers in the range below 100'000 g/mol (Table 3).

TABLE 2

Physico-chemical properties of the comb polyesters

| No | Polymer | PVADS[a] [%]/[mass %] | Backbone Mw[a][g/mol] | PLGA chain Mn[b][g/mol] | PLGA Units per Chain[b] | Polymer Mn[b][g/mol] | LA:GA[b] [mol %] | Best Solvent |
|---|---|---|---|---|---|---|---|---|
| 1 | PVA-g-PLGA | — | 15'000 | 4000 | 32 | 1'250'000 | 51:49 | DCM |
| 2 | PVA-g-PLGA | — | 15'000 | 1100 | 9 | 360'000 | 51:49 | 1:1(DCM:acetone) |
| 3 | PVA-g-PLGA | — | 15'000 | 590 | 5 | 238'00 | 50:50 | acetone |
| 4 | PVA-g-PLGA | — | 15'000 | 390 | 3 | 134'000 | 50:50 | acetone |
| 5 | PVA-g-PLGA | — | 15'000 | (50)* | (0.8)* | (30'000)* | (50:50)* | water |
| 6 | PVA-g-PLGA | — | 15'000 | (37)* | (0.4)* | (26'000)* | (50:50)* | water |
| 7 | PVA-g-PLGA | — | 15'000 | (30)* | (0.3)* | (24'000)* | (50:50)* | water |
| 8 | PVA-g-PLGA | — | 15'000 | (21)* | (0.2)* | (21'000)* | (50:50)* | water |
| 9 | P(SB-VA)-g-PLGA | 14/S = 6.8 | 19'900 | 590 | 5 | 172'000 | 53:47 | acetone |
| 10 | P(SB-VA)-g-PLGA | 14/S = 6.8 | 19'900 | (50)* | (0,4)* | (33'000)* | (50:50)* | water |
| 11 | P(SB-VA)-g-PLGA | 27/S = 10.0 | 26'000 | 840 | 7 | 210'000 | 52:48 | acetone |
| 12 | P(SB-VA)-g-PLGA | 27/S = 10.0 | 26'000 | (120)* | (2)* | (52'000)* | (50:50)* | 1:1(water:acetone) |
| 13 | P(SB-VA)-g-PLGA | 27/S = 10.0 | 26'000 | (60)* | (0.5)* | (35'000)* | (50:50)* | water |
| 14 | P(SB-VA)-g-PLGA | 43/S = 12.3 | 33'600 | 1100 | 9 | 221'000 | 53:47 | acetone |
| 15 | P(SB-VA)-g-PLGA | 43/S = 12.3 | 33'600 | (80)* | (0.6)* | (35'000)* | (50:50)* | water |

[a] = from elemental analysis
[b] = from NMR analysis
* = calculated from synthesis feeds since NMR signals were too broad for quantification Combined Size Exclusion Chromatography (SEC) and Static Light Scattering (SLS): 0.5% (w/v) polymer solutions were injected into a thermostatted (35° C.) Merck-Hitachi system with a differential refractometer (RI 71) and a MiniDawn light scattering detector (Wyatt Technology Corporation) (100 $\mu$l K5 cell, laser wavelength 690 urn, laser power 30 mW, three detecting angles (45°, 90° and 135°)). Chromatograms were obtained with degassed eluents at a flow rate of 1 ml/mm. For DCM and acetone, a Lichrogel PS mix and a PS 40 (10 $\mu$m) column (Merck) were used. For

TABLE 3

Light scattering analysis and intrinsic viscosities

| No* | Polymer | Mol. weight Mn[a] [g/mol] | Intr. Viscosity [dl/g] |
|---|---|---|---|
| 1 | PVA-g-PLGA01 | 1'563'000 | 0.61[b] |
| 3 | PVA-g-PLGA10 | 182'800 | 0.17[c] |
| 4 | PVA-g-PLGA30 | 140'400 | 0.11[c] |
| 5 | PVA-g-PLGA50 | 25'900 | — |

TABLE 3-continued

Light scattering analysis and intrinsic viscosities

| No* | Polymer | Mol. weight Mn[a)] [g/mol] | Intr. Viscosity [dl/g] |
|---|---|---|---|
| 6 | PVA-g-PLGA57.1 | 35'040 | 0.14[d)] |
| 7 | PVA-g-PLGA62.5 | 21'210 | — |
| 9 | P(SB(14)-VA)-g-PLGA10 | — | 0.20[c)] |
| 10 | P(SB(14)-VA)-g-PLGA50 | — | 0.14[d)] |

*numbers referring to table 2
[a)] from combined SEC and static light scattering analysis
[b)] DCM as solvent
[c)] acetone as solvent
[d)] aqueous 0.5 NaNo$_3$ solution Nuclear magnetic resonance spectroscopy (NMR) was performed at 35° C. with 6% (w/v) polymer solutions in different fully deuterated solvents (such as d$_6$-acetone, CDCl$_3$, d$_6$-DMSO, and D$_2$O). 400 MHz $^1$H- and 100 MHz $^{13}$C-NMR spectra were recorded with a Jeol GX400 Delta N FT spectrometer, 500 MHz $^1$H- and 125 MHz $^{13}$C-NMR spectra with a Jeol LA500 eclipse+Delta FT spectrometer.

Figure 4:
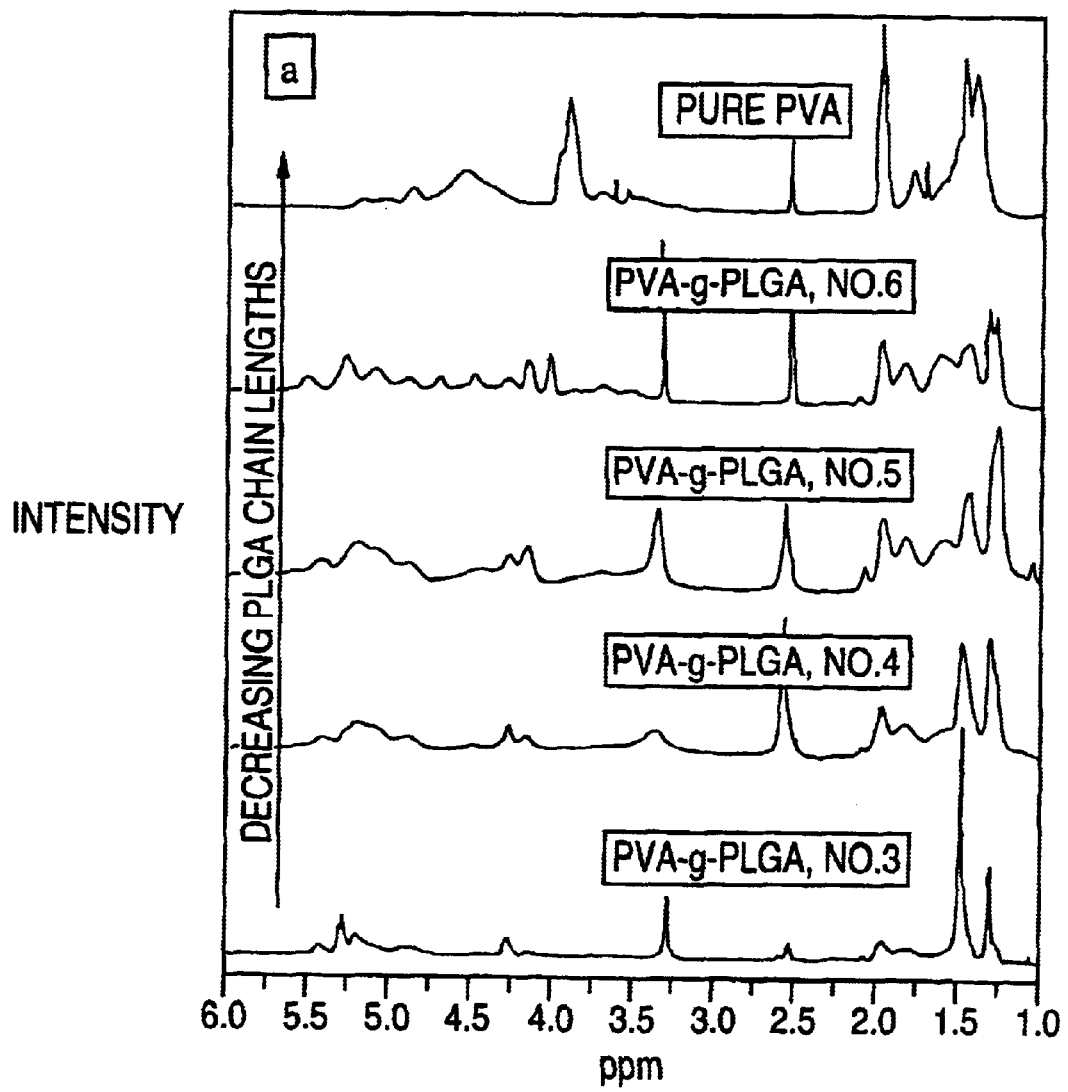
FIG. 4: Shows polymer $^1$H NMR spectra as a function of PLGA chain lengths.

As shown in FIG. 4, the reduction of the side chain lengths is manifested by a decrease in the intensity of the PLGA chain $^1$H NMR signals (1.45 ppm=lactic acid methyl groups, 4.8 ppm=glycolic acid methylene groups, and 5.16 ppm=lactic acid methine groups) and accordingly an increase in the intensity of the hydroxyl terminated PLGA end groups (4.2 ppm=terminal —CH$_2$OH, 4.35 ppm= terminal —CH(CH$_3$)OH, and 1.28 ppm=terminal —CH (CH$_3$)OH). The PVA signals were found at 1.9 ppm=OCO—CH$_3$, 1.7 ppm=CH—OCO, and in the region of 1.3 to 1.5 ppm=CH$_2$. By comparing the signal intensities of the PLGA chain and end groups, the average PLGA chain lengths could be calculated.

Intrinsic viscosities were determined with an Ubbelohde viscosimeter (Schott Geräte, Germany) from aqueous 0.5 N NaNO$_3$ solutions at 25° C. with at least four different concentrations.

Surface Tensions (σ) were analyzed in triplicate with a tensiometer from MGW Lauda according to the DuNoüy ring method with at least eight different concentrations of aqueous polymer solutions at 25° C. Surface pressure (p)was calculated according to the following equation:

$$p(\text{sample}) = \sigma(\text{Water}) - \sigma(\text{sample}).$$

Turbidity measurements as a function of temperature for LCST determination were preformed at different wavelengths with a Shimadzu UV-VIS spectrophotometer UV-160 or with a Zetasizer 4 (AZ110 cell, Malvern Instruments, 630 nm, 90°).

Figure 5:
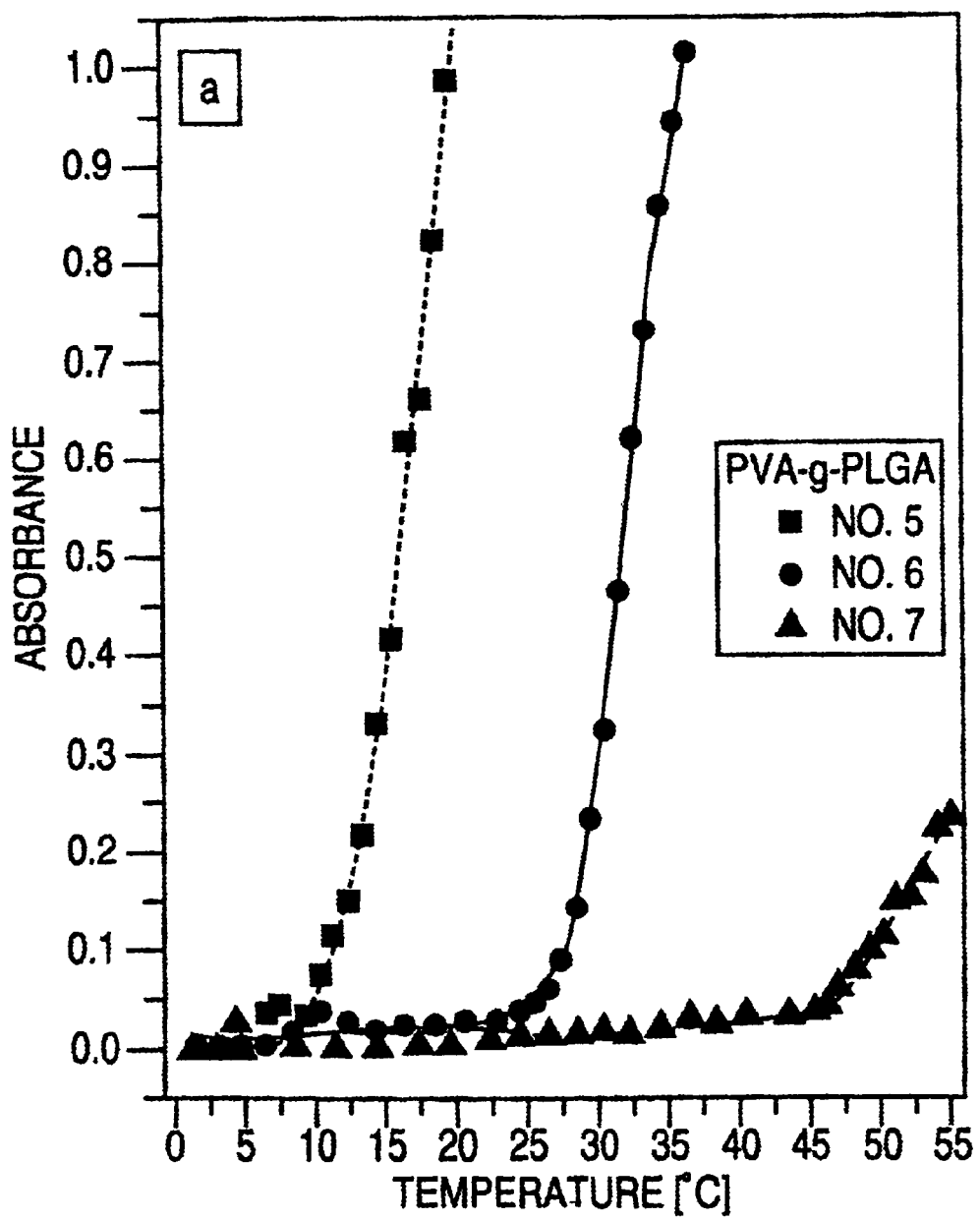
FIG. 5: Shows a plot of the turbidity of polymer solutions plotted against temperature.

Turbidity of the polymer solutions is plotted against temperature in FIG. 5. In addition, LCST (as turning point of the slopes) was also a linear function of the PLGA chain lengths, just as all other physicochemical properties. A lower critical solution temperature (LCST), polymer precipitation at higher temperatures, was found.

Figure 6:
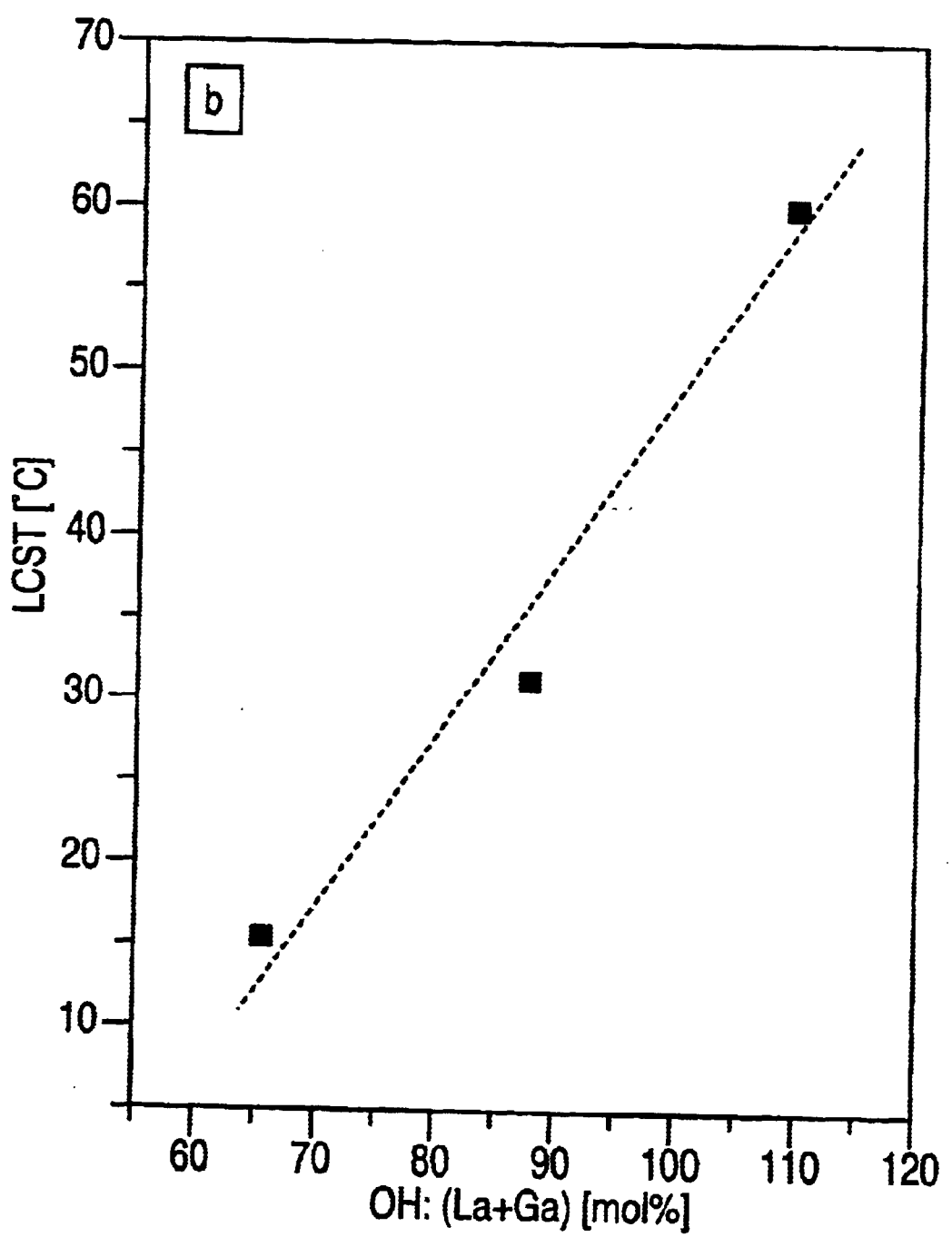
FIG. 6: Shows a plot of LCST as a function of PLGA chain lengths.
Figure 7:
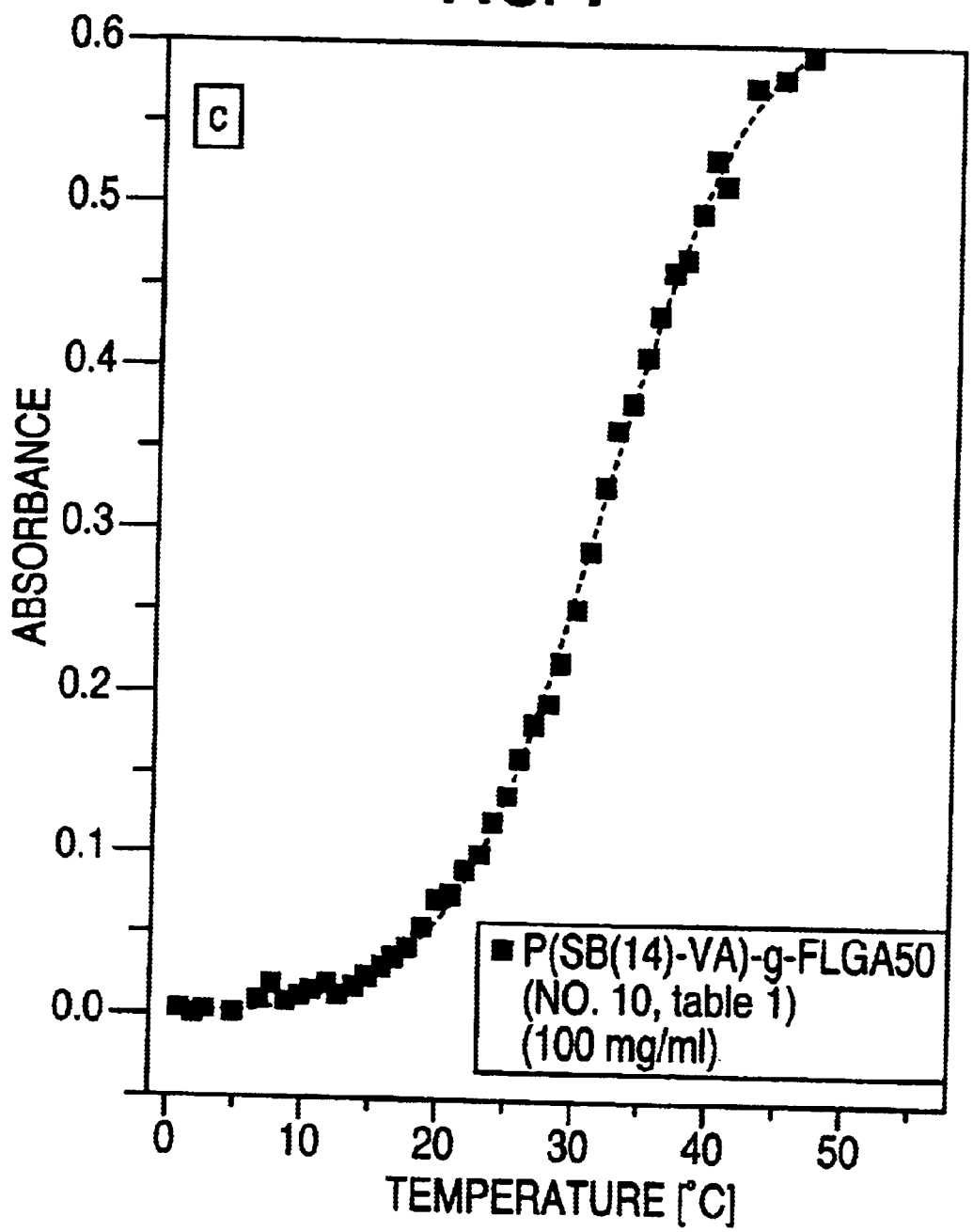
FIG. 7: Shows a plot of the turbidity of polymer solutions plotted against temperature.

The shorter the side chains, the more polyol like the polymers and, therefore, the better their solubility, causing higher precipitation temperatures (FIG. 6). Nevertheless, these temperatures were in a quite attractive range near physiological conditions. At high polymer concentrations, temperature-induced precipitation was even visible for polymers with an anionic backbone (FIG. 7), although they generally exhibited better solubility owing to the charged groups, which raised LCST to high values. The existence of a LCST offered a first novel possibility to a prepare hydrogel type of protein delivery system with these polyesters: combining a protein and a polymer solution, then raising the temperature above LCST, e.g. by parenteral application, resulted in polymer aggregation and precipitation partially including protein molecules.

EXAMPLE 2

The purpose of this example was to demonstrate preparation and characterization of polymer/protein complexes.

Preparation (compare Table 5, below). 100 mg of polymer were dissolved in 1 ml of an isotonic (0.15 M) phosphate buffer saline solution (PBS) of knon pH. In a typical example, 100 µl of this polymer stock solution was transferred into a 1500 ml Eppendorf vial and diluted with 800 µl of PBS. Finally, 100 µl of a 10 mg/ml protein stock solution in PBS was added and vortexed for 10 seconds.

Each experiment was performed in triplicate. For the use of uncharged polymers, the temperature was raised from room temperature to 37° C. for 1 hour.

Drug loading and release (at 37° C.) were determined after centrifugation of the complexes in the supernatant photometrically at 280 nm (Ttx) and 491 nm (FITC-BSA) with a Shimadzu UV-VIS spectrophotometer UV-160 in triplicate. Complexes containing FITC-BSA were optically investigated with a Standard Fluorescent Microscope (Zeiss, Germany) equipped with a Zeiss 490/525 nm FITC-filter.

For visualization of the colloid morphology freshly prepared complexes were cast on silicon wavers and allowed to dry at room temperature for three days. Then they were investigated with a field emission scanning electron microscope S-4100 (Hitachi) or a SEM CamScan 4 (Elektron-Optik Service GmbH, Germany) equipped with a Voyager EDX analyzer (Noran Instruments, USA) with an ultra thin window enabling the detection of light elements. Freeze-fracturing samples were applied in the hole of a pair of gold specimen holders, snap-frozen in nitrogen slush (−210° C.), and transferred to a freeze-fracturing apparatus (BAF 400 D, Balzer) equipped with an oscillating quartz monitor (QSG 301). The samples were fractured at about $5.10^{-6}$ mbar and shadowed immediately with platinum (2 nm, 45°) and-carbon (20 nm). The replicas were cleaned in 6% sodium hypochlorite for 1 hour, washed with water several times, and mounted on copper grids. Transmission electron microscopy was performed with a Zeiss EM 10.

While in case of the uncharged polymers larger inclusion-like aggregates with e.g. fluorescently labeled bovine serum albumin (FITC-BSA) using the temperature switch were observed, the situation changed when a negatively charged polymer and a protein solution were combined. In this case, temperature independent spontaneous self-assembly of much smaller complexes occurred. In both experiments small dot-like fluorescence accumulation was visual, while in case of a pure protein solution as a control only weak indifferent fluorescence occurred. These observations could be confirmed by various high-resolution microscopic techniques, such as field emission scanning electron and freeze fracture transmission electron microscopy. The anionic polymers yielded very small colloids with sizes of only a few hundred nm, while larger precipitates in the µm-range were found in case of the uncharged polymers.

Colloid sizes and distributions were measured at 25° C. in aqueous dispersion (200 µg/ml) by photon correlation spectroscopy (PCS) with a Zetasizer 4 (AZ110 cell, Malvern Instruments) in triplicate (90° sample time 120 µs, serial mode, 4 mW laser, 64 channel correlator, multimodal analysis).

Isothermal titration calorimetry (microcalorimetry) was performed with an MCS-ITC instrument (Microcal Inc) (25° C., cell volume 1351.3 $\mu$l, stirring syringe 250 $\mu$l, 400 rpm, 10 $\mu$l injections every 250 sec.) and data processing with the software Origin 3.5 (Microcal). Polymer solutions of known concentration were titrated at different pH solutions with protein solutions of known concentration (compare Table 5, below). All experiments were corrected by measured values of dilution enthalpy.

Non-reducing SDS PAGE and Native PAGE experiments were carried out with a PhastSystem (separation and development unit, LKB Pharmacia). Protein separation and gel development was performed with the Pharmacia methods 'separation' and 'development technique files.' For protein separation, 1 $\mu$l of the sample was applied onto foil supported poly(acryl amid) gels (PhastGel gradient 8–25, SDS-PAGE: PhastGel SDS buffer strips, Native PAGE: PhastGel Native buffer strips, Pharmacia). For calibration a high and low molecular weight kit for electrophoresis (Pharmacia) were used. After electrophoresis, staining was performed with Coomassie Blue (PhastBlue R, Pharmacia), residual dye was removed by washing with a mixture of methanol:acetic acid:water (3:1:6), and then the gels were fixated.

For statistical design and analysis (factorial screening design with 3 centerpoints) the software STATGRAPHICS Plus for Windows 2.1 (Statistical Graphics Corp., Rockville, U.S.A.) was used.

The complex composition was investigated after purification and isolation by several centrifugation and washing steps. The presence of the polymer could be easily detected by $^1$H NMR analysis after complex redissolving in deuterated DMSO (data not shown). The presence of the protein, in this case iron containing cytochrome C (CytC), was confirmed with an electron microscope equipped with energy dispersive x-ray microanalysis (EDX) successfully allowing the detection of the protein iron atom in the complexes at ca. 6.25 to 6.5 keV.

Figure 8:
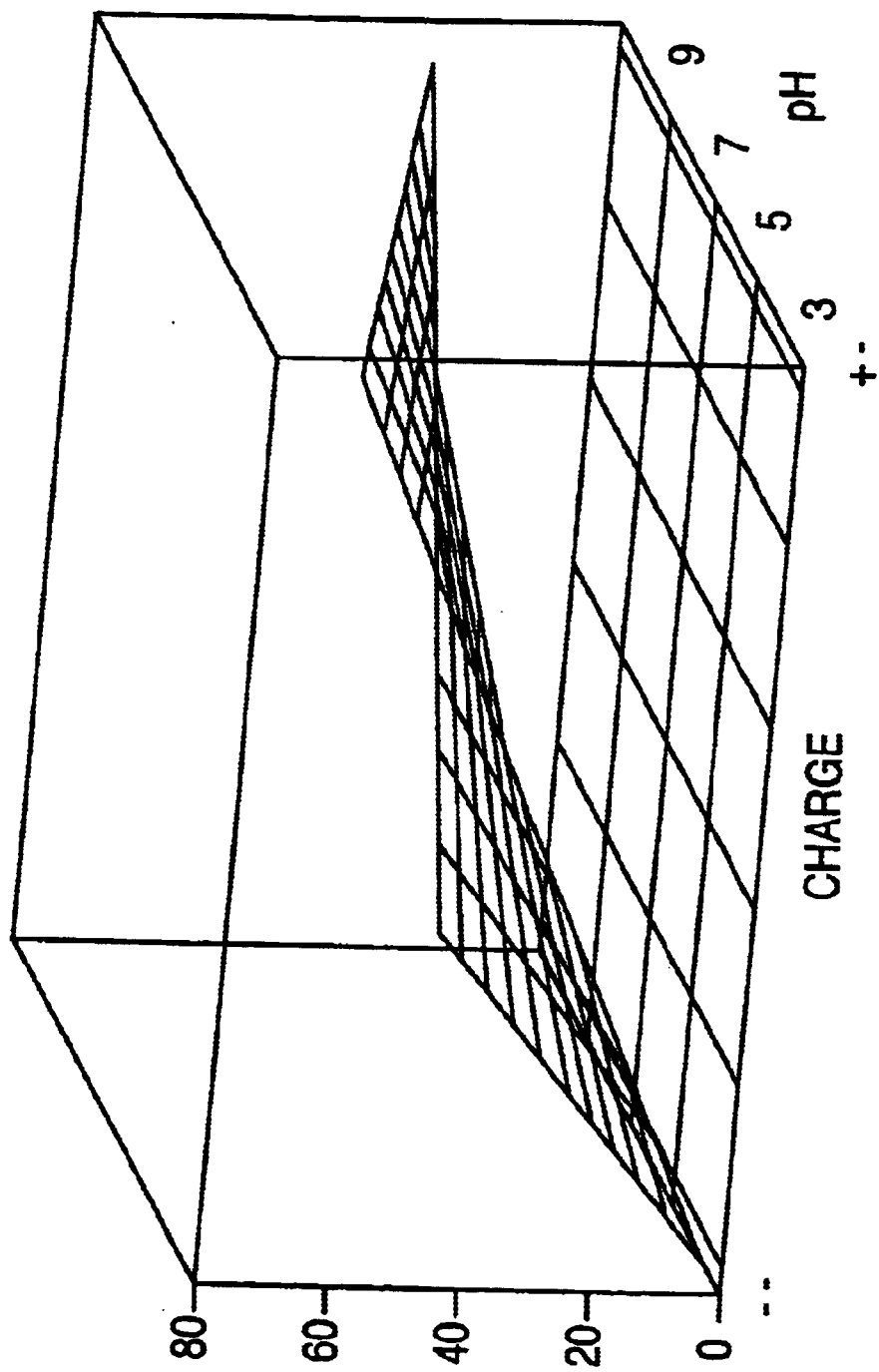
FIG. 8: Shows dynamic laser light scattering (DLS) intensity of complexes of charged dextrans and an anionic polymer.
Figure 9:
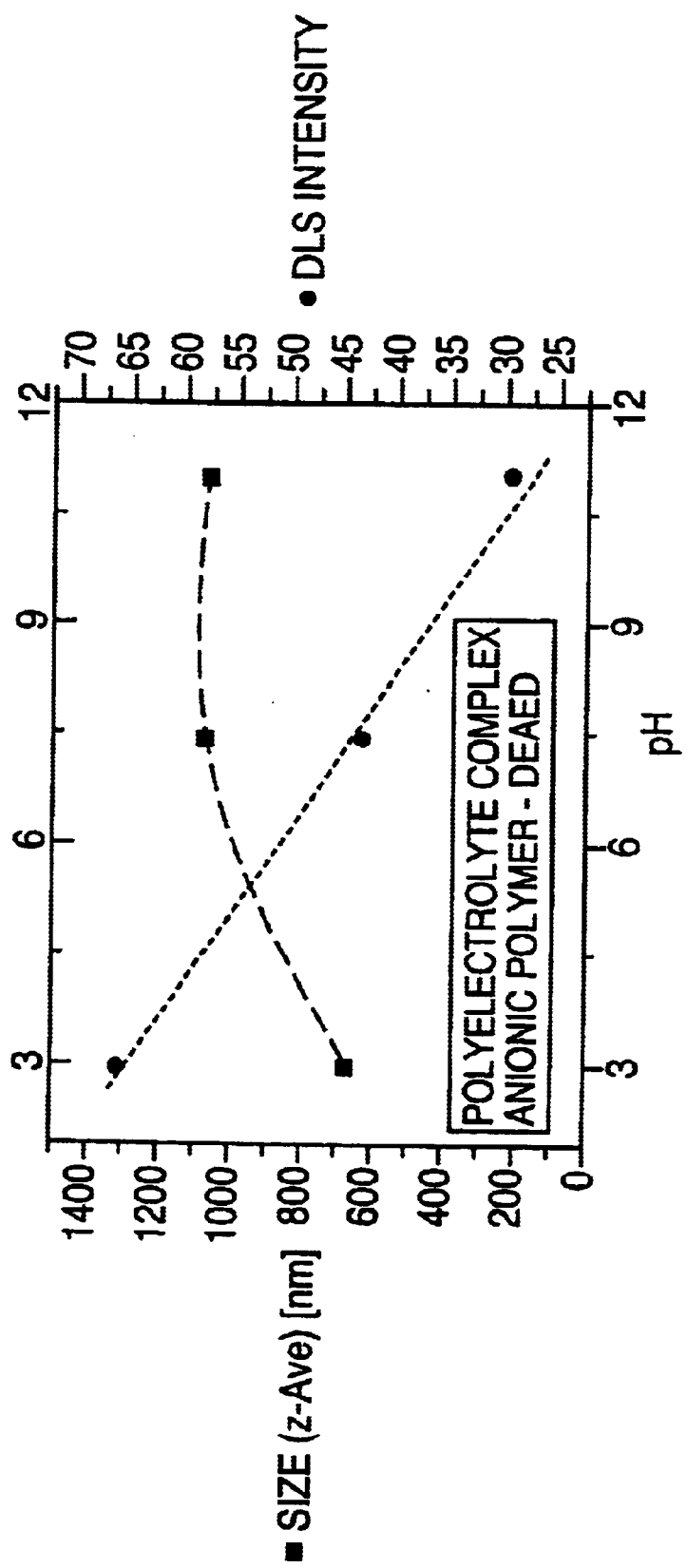
FIG. 9: Shows sizes as a function of complexes of charged dextrans and an anionic polymer.

To prove the complexation character of the spontaneous self-assembly seen with the anionic polymers, their reaction with a positively and a negatively charged dextran, diethylaminoethyl-dextran (DEAED) and dextran sulfate sodium (DSS), was investigated as a function of solution pH by dynamic laser light scattering (DLS). As shown in FIG. 8, the two negative partners did not interact in any way.

The solutions stayed clear and showed neither Tyndall effect nor turbidity at all. In contrast, a distinct increase of DLS intensity indicated the spontaneous complex formation between the anionic polymer and the cationic poly (saccharide). Moreover, this reaction was strongest at pH 3, linearly decreasing with increasing pH values, indicating the role of the charged groups in the polymer backbone, which become saturated and neutralized at higher pH.

Figure 10:
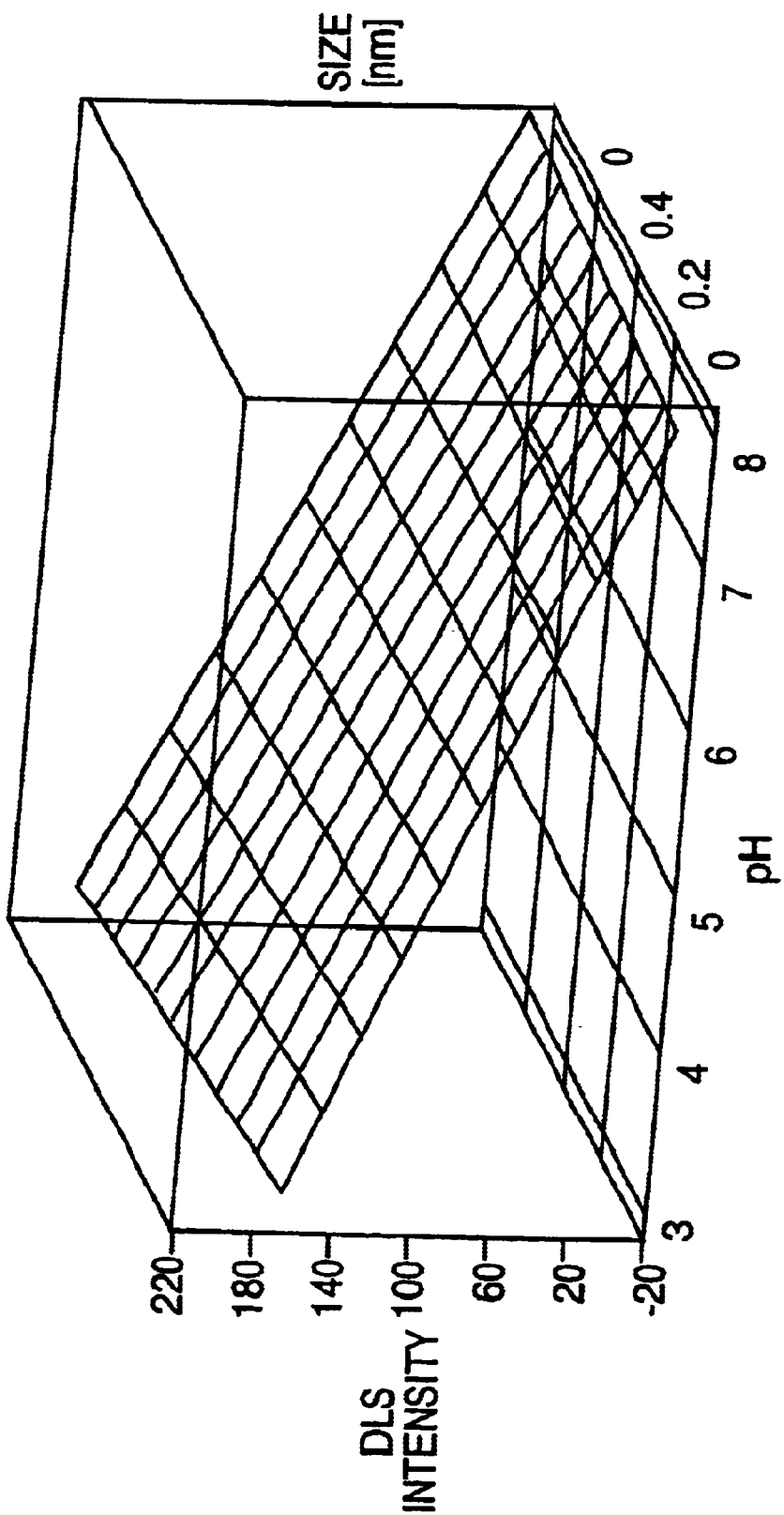
FIG. 10: Shows the effect of solution pH on the DLS intensity of complexes of BSA and an anionic polymer.
Figure 11:
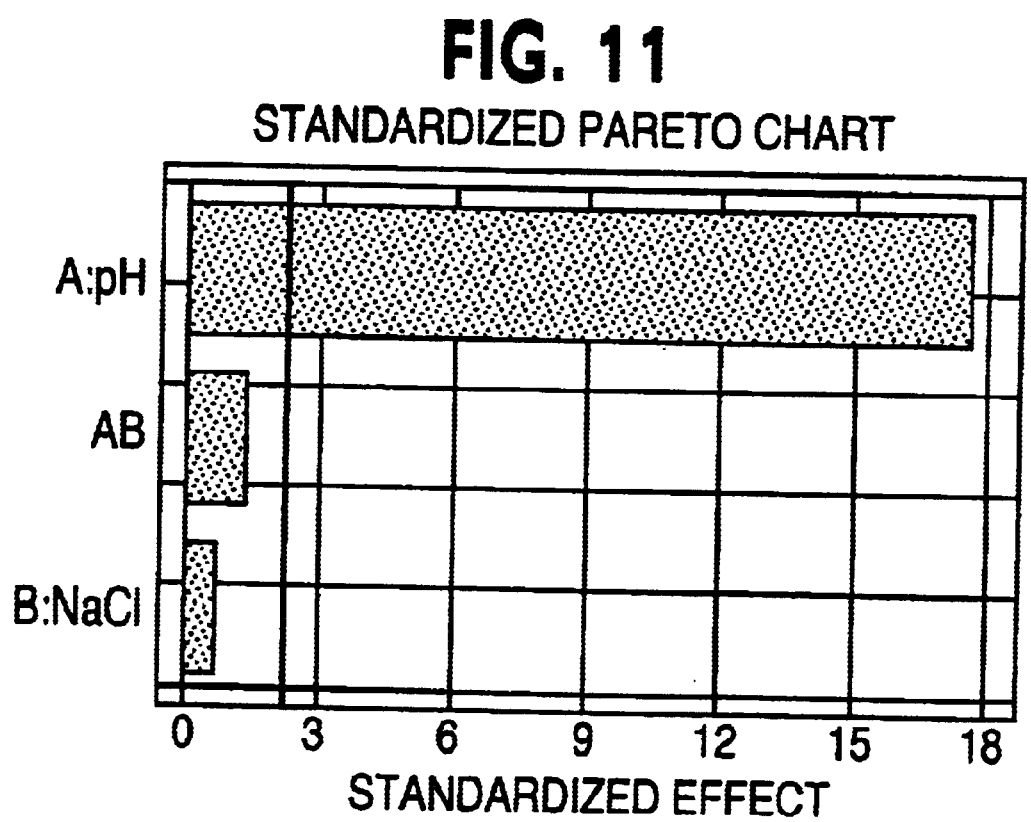
FIG. 11: Shows the effect of ionic strength on the DLS intensity of complexes of BSA and an anionic polymer.

Applied to a protein in solution a pH above its point of isocharge (PI) will cause a negative overall charge, and similar to the anionic dextran no complexation should occur. At a pH below its PI it should be able to interact with the negative polymer due to its positive charge. The sulfonic acid group of the polymer is a very strong acid and will be dissociated over a broader pH range, enabling the complexation of a wide variety of proteins with different PI values. In FIGS. 10 and 11, a factorial experimental design show this expected influence of solution pH and ionic strength (amount of additional NaCl) on the complexation reaction of BSA and an anionic polymer at a constant polymer to protein ratio. The DLS intensity, as an indirect measure of number (and sizes) of the formed polyelectrolyte complexes between polymer and protein, decreased with increasing pH value. The strongest reaction was seen at the lowest pH investigated (pH 3), where the polymer is negatively and the protein positively charged. The intensity was significantly decreasing at a pH near the PI of the protein, where its overall charge is zero, further decreasing with increasing solution pH. At about pH 6–7 no reaction was observable.

These results demonstrate one of the major advantages: if applied parenterally, the negative charge of the polymer and moderate pH in the range of physiological conditions will prevent complexation of serum albumin being anionic itself.

Figure 12:
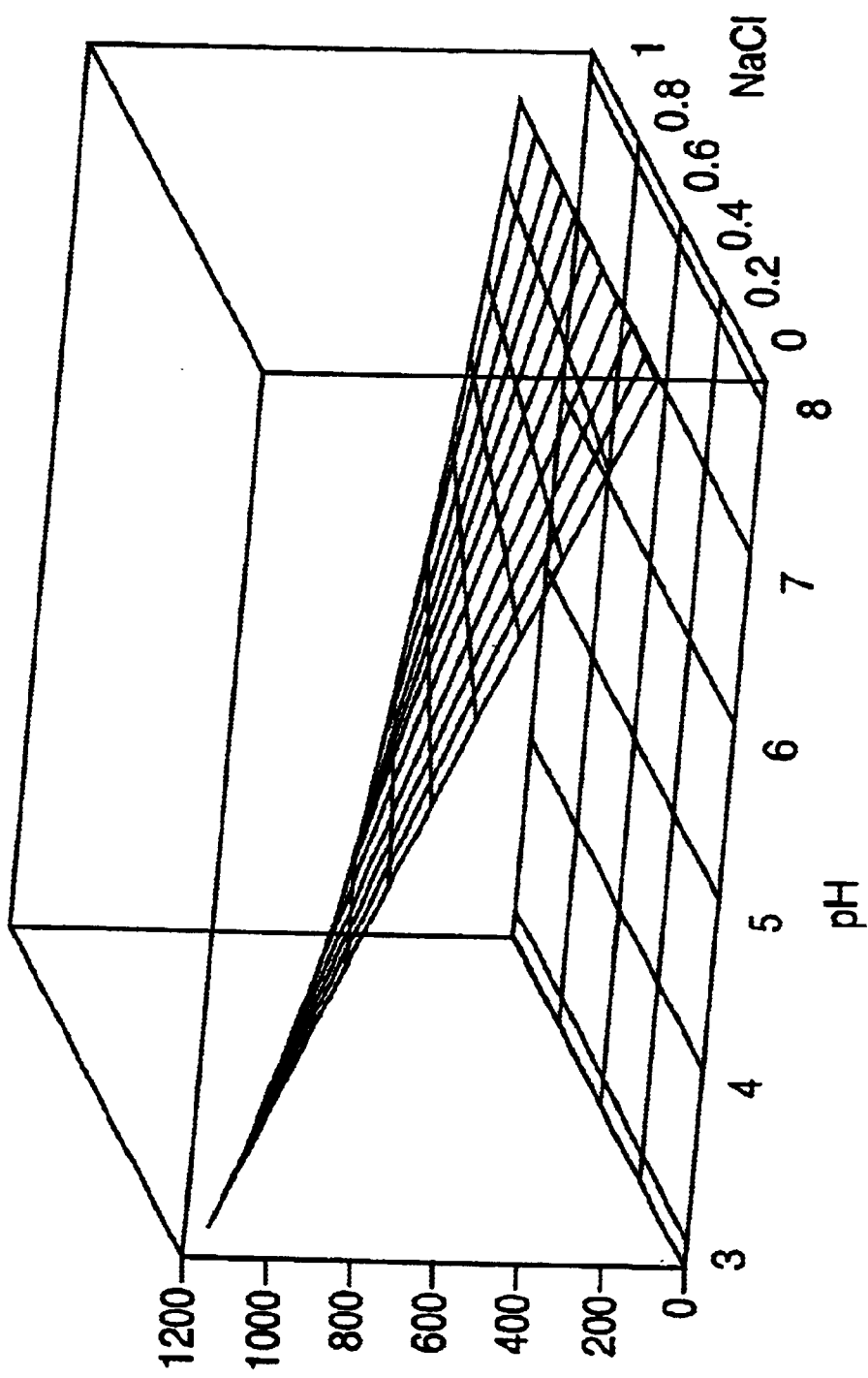
FIG. 12: Shows the effect of solution pH on the sizes of complexes of BSA and an anionic polymer.
Figure 13:
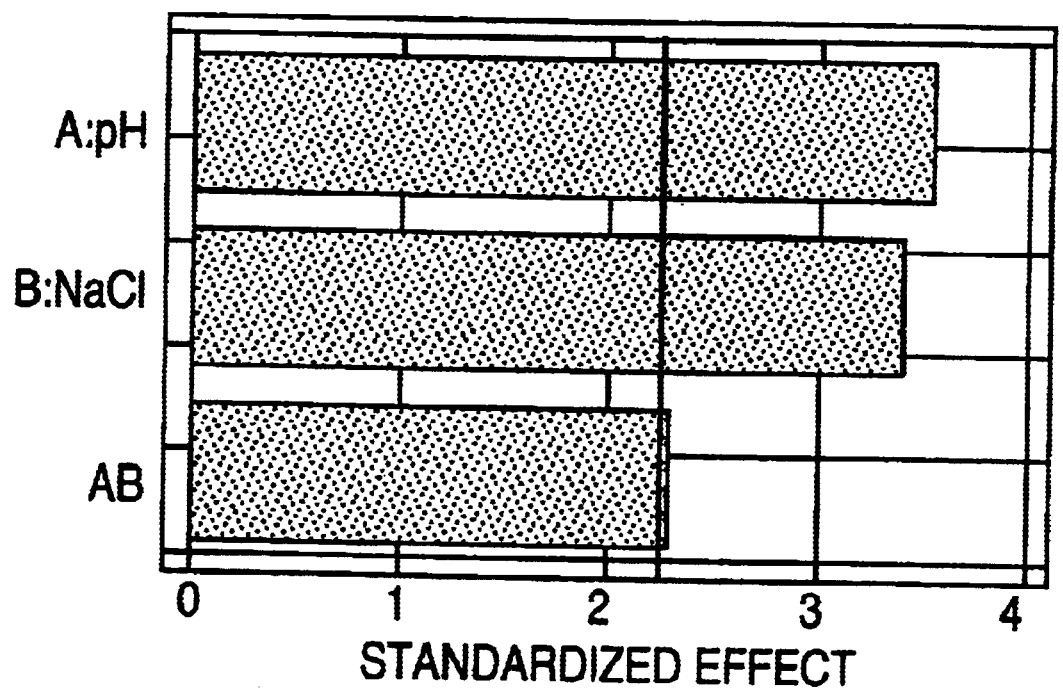
FIG. 13: Shows the effect of ionic strength on the sizes of complexes of BSA and an anionic polymer.

While the ionic strengths of the buffers used had no major influence on the DLS intensity—the pure complex formation—distinct dependency on the amount of additional NaCl was found for the sizes of the self-assembled colloids. See FIGS. 12 and 13. Especially at low pH up to values near the PI of BSA this effect was strongest. The sizes were decreasing with increasing ionic strengths, which can be explained by the high affinity of small ions to the charged group of the polymer as well as the protein. At the examined ratio of polymer to protein (10:1 w/w), an excess of polymer, the overall charge of the complexes seemed to be not completely saturated. This could lead to secondary aggregation between the complexes themselves and, thereby, cause larger aggregate sizes. This effect of course will occur to a less degree, if the charges are masked by small counterions to some extent. Drug loading was equally a linear function of solution pH, while no influence of the ionic strength of the solution was observed. The highest loading were achieved under acidic conditions linearly decreasing with increasing pH, reflecting the results on complex formation and sizes. Investigation of the complex stability by supplementary addition of sodium chloride to increase the solution ionic strengths after complex formation revealed no major changes. Neither colloid sizes nor DLS intensity were influenced, except for the dilution effect, indicating the very strong bonding between the complex partners. Being able to control the number of sizes as well as, therefore, the drug loading of the complexes by factors, such as solution pH and ionic strengths, will be another advantage in controlled drug delivery. It is well known that especially small particles are most effective in e.g. mucosal (oral, nasal) application.

If an excess amount of polymer was used, the polymer to protein ratio had no significant influence on the colloid sizes. Ratio-independent sizes in the range of 200 to 300 nm were observed for CytC complexes, if solution pH was kept clearly below the proteins PI. Moreover, under these conditions it was always possible to achieve effective drug loadings in the range of 90 to 100% of the protein amount. These results gave first evidence for a stoichiometric reaction, which could be confirmed by the yields, determined after centrifugation, washing and drying. Yields were linearly increasing with the more protein present. Even with the inclusion-like complexes prepared from the uncharged polymers above, their LCST in the range of 1 to 20% (mass protein/polymer), 80% of the protein were coprecipitated in these hydrogels.

To further investigate the nature of the reaction between the polymers and the proteins, isothermal titration calorimetry (ITC) was performed. Polymer solutions of known concentration and pH were degassed and titrated with protein solutions under stirring at constant temperature. The resulting heat changes after each injection were determined against a water filled reference cell. Titration of the uncharged polymers with proteins revealed no major heat changes except dilution effects, indicating that at constant temperature below polymer LCST nearly no reaction occurred. Similar results were reported for PVA and alkylated PVA hydrogels, investigated by monolayer method.

Figure 14:
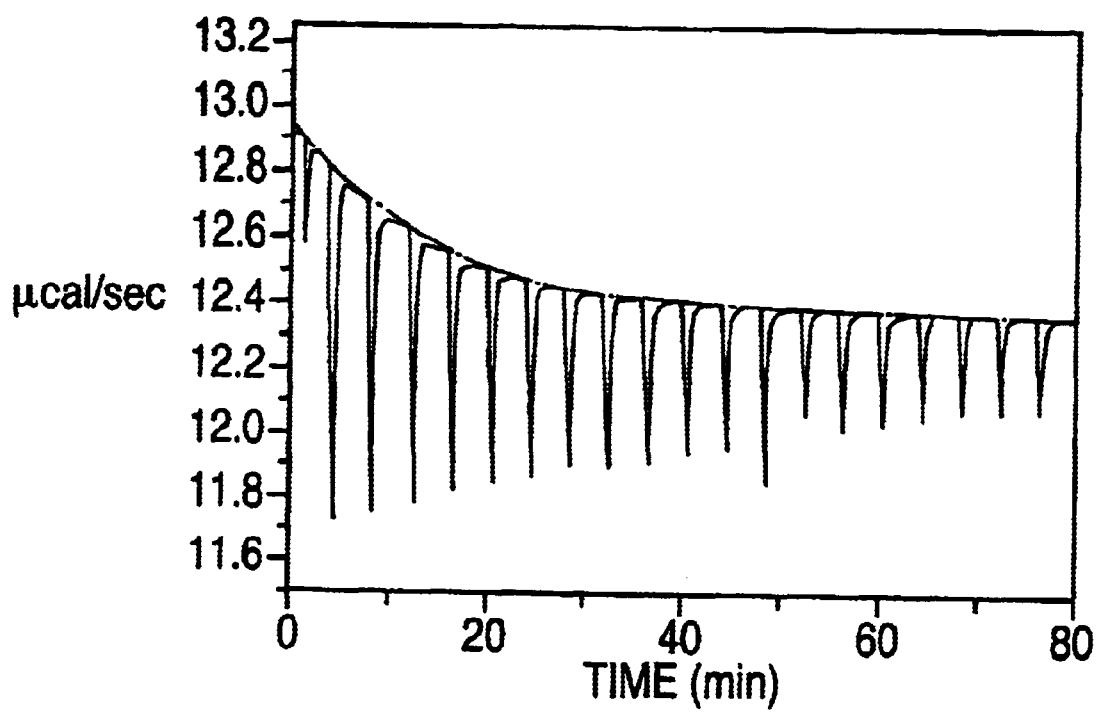
FIG. 14: Shows heat changes as a result of complexation between a negative polymer and a protein upon successive protein injections.
Figure 15:
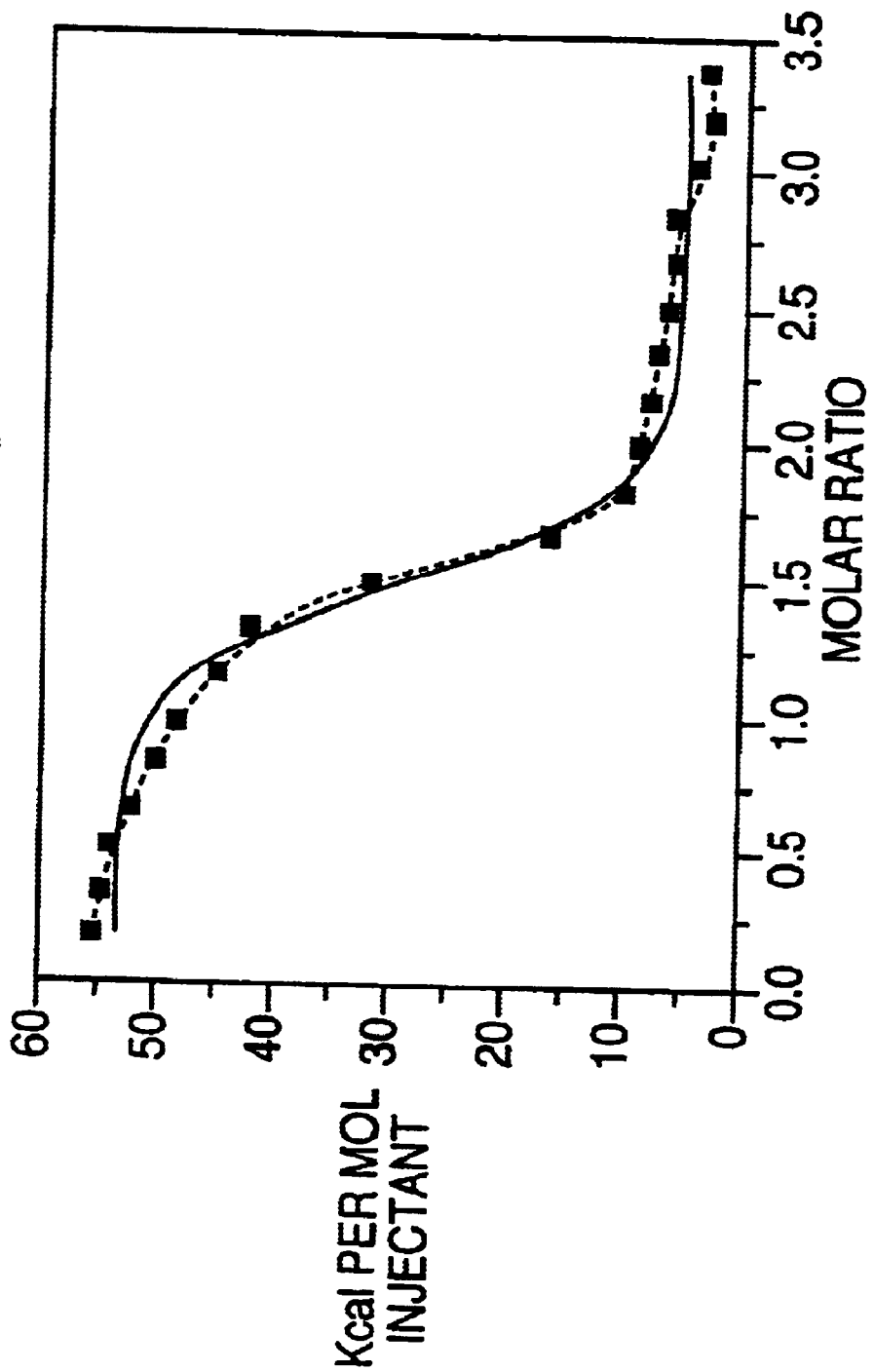
FIG. 15: Shows a plot of the energy changes derived from titration experiments after subtracting the heat of dissolution of the protein in buffer.

For the negative polymers, strong heat changes during titrations were observed, due to the complexation reaction. The heat changes associated with the complexation were endothermic and decreased monotonically upon successive protein injections as outlined in FIG. 14. After about 10 injections the heats became the same as those observed for the dilution of the protein in pure buffer. FIG. 15 gives a typical example of the obtained plot of the energy changes derived from the titration experiments after subtracting the heat of dissolution of the protein in buffer. These plots allowed the determination of the heat of complexation (first plateau of the slopes) and the stoichiometry of the reaction (turning point of the slopes). These results are in reasonable agreement with literature data, e.g. the adsorption of albumin onto negatively charged surfaces. Duncan et al., "Effect of C4-, C8- and C18-alkylation of Poly(vinyl alcohol) Hydrogels on the Adsorption of Albumin and Fibrinogen from Buffer and Plasma: Limited Correlation with Platelet Interactions," *Biomat.*, 18:1585–1592 (1997); Norde et al., "The Adsorption of Human Plasma Albumin and Bovine Pancreas Ribonuclease at Negatively Charged Polystyrene Surfaces, V. Microcalorimetry," *J. Colloid and Interface Sci.*, 66(2):295–302 (1978); and W. Norde, "Adsorption of Proteins from Solutions at the Solid-liquid Interface," *Adv. Colloid and Interface Sci.*, 25:267–340 (1986).

Figure 16:
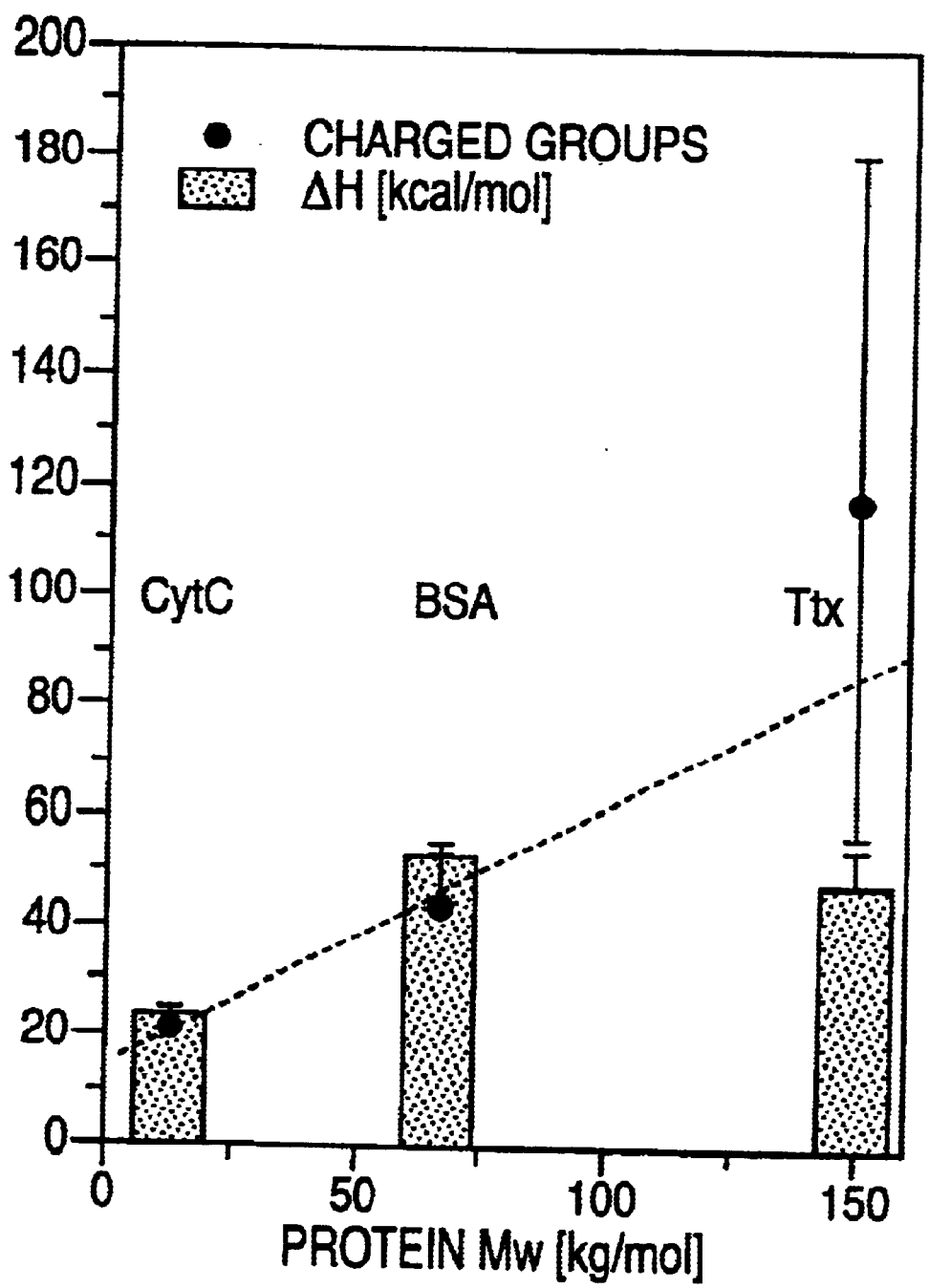
FIG. 16: Shows the results of a series of experiments with different proteins (CytC, BSA, and tetanus toxoid (Ttx)) to determine the dependency of the complex composition and the size/molecular weight.

The complexation is driven by a large increase in entropy, which can be explained by the release of a high number of water molecules, dehydration of the macromolecules during contact formation. From a series of experiments with different proteins a dependency of the complex composition and the size/molecular weight of the protein was found (FIG. 16), already postulated from the drug loading results described above. It is worth noting, that the mean values and standard deviations in this plot are not derived by repeating a single experiment for several times, but by a series of experiments using different concentrations of the two complex partners.

For 12'000 g/mol CytC, two protein molecules seem to share one polymer molecule, which in the plot expressed by the amount of charged group present in the backbone. One polymer contains about 42 sulfobutyl groups, two molecules about 84, etc. For the complexation of a single CytC molecule, about 20 of the 42 charged groups of one polymer seemed to be necessary. A 1:1 reaction was found for BSA and a 2:1 reaction for tetanus toxoid (Ttx), with an approximate Mw of ca. 150'000 g/mol. In other words, a maximum drug loading of 50% (w/w) for Ttx could be achieved, for BSA 100% (w/w), and even 200% (w/w) in case of CytC, demonstrating the potential of this type of drug delivery system, especially compared to microspheres, which normally enable drug loadings in the range of about 1 to 10%.

Drug Release and Stability. To investigate the influence of pH on the complex stability and protein decomplexation, drug release, a series of FITC-BSA complexes was prepared at pH 3 and purified by three centrifugation/washing cycles. The purified samples were then immersed in buffer solutions of different pH (3, 6, 7.4) at 37° C. At pH 3 negligible protein release was observed. The complexes once prepared remain stable for at least for several days. Raising the pH to 6 resulted in a slow but continuous release of the complexed protein. A further increase of pH to physiological conditions (PBS 7.4) caused a fast and nearly linear release of the complete protein amount in less than 24 hours.

The released proteins were investigated after centrifugation in the supernatant with regard to their stability by native and SDS poly(acryl amide) gel electrophoresis (PAGE). Compared to the original protein they were still in a non-aggregated, native form. The complex formation obviously was fully reversible, the presence of the polymers successfully inhibited protein self-aggregation and denaturation even under very acidic conditions and at elevated temperatures.

Figure 17:
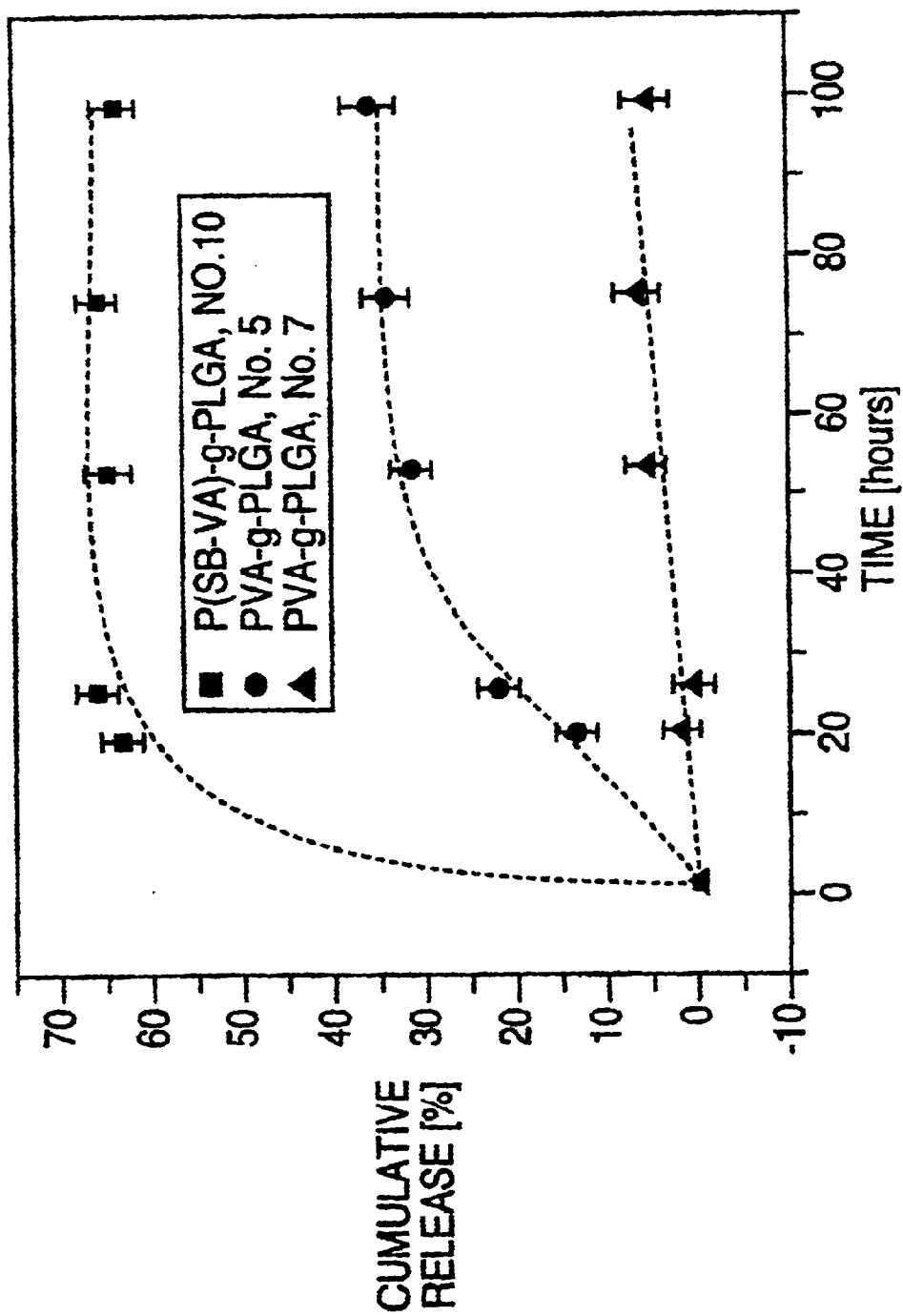
FIG. 17: Shows the release of Ttx as a function of complex polymer type.

Comparable results were obtained with tetanus toxoid containing colloids (FIG. 17). No release at acidic pH, significantly accelerated at pH values above the PI of the protein. The release from the inclusion-like complexes with uncharged polymers was found to be pH independent and much slower. It seemed to be mainly an adsorption/desorption equilibrium, controlled by the polymer composition. Higher amounts of the hydrophilic backbone in the polymer (equal to shorter PLGA chains) enabled slightly faster release through the porous hydrated PVA domains, while in case of higher Mw polymers release rates were reduced.

Possible Applications. Bioadhesion might be one useful property of the complexes, since the polymers themselves were found to possess surface activity. Determination of the surface pressure and the CMC as outlined in Table 4, below, showed that the comb polyesters still exhibited values quite comparable to the polyol backbones themselves, which are known for their surfactant-like properties. Therefore, the polyelectrolyte complexes might be a potential tool for mucosal vaccination. Moreover, protein complexation seemed to increase protein stability and, therefore, could possibly alter its bioavailability and biodistribution in parenteral application.

TABLE 4

Surface activity of the polymers

| Backbone | Surf. Pressure [mN/m] | CMC [mmol] |
|---|---|---|
| PVA | 27.5 | 0.89 |
| SB(14)PVA | 18.8 | 0.57 |
| PVA-g-PLGA | 27.8 | 0.42 |
| SB(14)PVA-g-PLGA | 28.1 | 0.58 |

TABLE 5

| Experiment | Polymer concentration | Protein concentration | Preparation Buffer/Volume | FIG. |
|---|---|---|---|---|
| Visualization | PVA-g-PLGA57.1 (No 6, tab. 1)<br>P(SB(14)-VA)-g-PLGA50 (No 10, tab. 1)<br>10 mg/ml | FITC-BSA - 1 mg/ml | PBS 3, 1000 µl | |
| | PVA-g-PLGA57.1 (No 6, tab. 1)<br>SB(14)PVA-g-PLG_50 (No 10, tab. 1)<br>10 mg/ml | CytC - 1 mg/ml | PBS 3, 1000 µl | |
| | P(SB(14)-VA)-g-PLGA50 (No 10, tab. 1)<br>10 mg/ml | BSA - 1 mg/ml | PBS 3, 1000 µl | |

TABLE 5-continued

| Experiment | Polymer concentration | Protein concentration | Preparation Buffer/Volume | FIG. |
|---|---|---|---|---|
| Complexation | P(SB(14)-VA)-g-PLGA50 (No 10, tab. 1) 10 mg/ml | DSS - 1 mg/ml DEAED - 1 mg/ml | PBS 3, PBS 7.4, PBS 9 1000 µl | 8, 9 |
| | P(SB(14)-VA)-g-PLGA50 (No 10, tab. 1) 10 mg/ml | BSA -1 mg/ml | PBS 3, PBS 7.4, PBS 9 +0.25M NaNO3 +0.50M NaNO3 +1.00M NaNO3 1000 µl | 10–13 |
| Size Drug loading | P(SB(14)-VA)-g-PLGA50 (No 10, tab. 1) compare figure 10 mg/ml | CytC, compare figure BSA, 0.66 mg/ml | PBS 3, PBS 5, 500 µl PBS 4, 1000 µl | |
| | P(SB(14)-VA)-g-PLGA50 (No 10, tab. 1) 10 mg/ml | BSA, compare figure | PBS 3, 1000 µl | |
| Microcalorimetry | P(SB(14)-VA)-g-PLGA50 (No 10, tab. 1) 0.5 mg/ml, 1 mg/ml, 2 mg/ml, 4 mg/ml 0.5 mg/ml, 1.25 mg/ml 1.25 mg/ml, 2.5 mg/ml, 5 mg/ml | CytC - 10 mg/ml BSA - 10 mg/ml tetanus toxoid - 16.6 mg/ml | PBS 3 (PBS 5) PBS 3 + 0.25M NaNO3 PBS 3 + 0.50M NaNO3 | 14–16 |
| | PVA-g-PLGA57.1 (No 6, tab. 1) 1.25 mg/ml, 2.5 mg/ml, 5 mg/ml | BSA - 10 mg/ml | | |
| Drug loading and release | P(SB(14)-VA)-g-PLGA50 (No 10, tab. 1) 10 mg/ml | FITC-BSA - 1 mg/ml | Preparation in PBS 3/1000 µl Release in PBS 3, PBS 6, PBS 7.4 | |
| | P(SB(14)-VA)-g-PLGA50 (No 10, tab. 1) PVA-g-PLGA50 (No 5, tab. 1) PVA-g-PLGA62.5 (No 7, tab. 1) 10 mg/ml | tetanus toxoid -2 mg/ml | Preparation in PBS 4/1000 µl Release in PBS 6 | 17 |

EXAMPLE 3

The purpose of this example was to determine the bioadhesive properties of the polymer compositions of the invention.

Bioadhesion was investigated by cell culture incubation experiments. Caco-2 cell monolayers were used as an in vitro tool to assess the binding of these complexes to intestinal epithelium. This well characterized model of the human intestinal mucosa has been widely used to study NP and antigen interactions due to its similarity to absorptive intestinal cells.

Caco-2 cells were cultivated and seeded onto poly (carbonate) membranes (Costar, Transwell Cat. 3412) according to Jung et al., "Oral and Nasal Administration of Tetanus Toxoid Loaded Nanoparticles Consisting of Novel Charged Biodegradable Polyesters for Mucosal Vaccination," *Proc. Int. Symp. Control. Rel. Bioact. Mater.*, 26:5021(1999). The cell monolayer was incubated for two hours with an initial concentration of (2000: 50)µg (polymer: protein)/ml, then washed three times with PBS 7. After fixation it was investigated with CLSM or TEM imaging.

Cells were used for experiments between day 20 and 22 postseeding. Monolayers grown on permeable filter inserts were preincubated in HBSS for 30 mm and 1.5 ml of the appropriate complex dispersion containing 2 mmol TRH as a permeability marker were applied to the luminal and 2.6 ml HBSS to the basolateral side. After predetermined time intervals of up to 120 min., 1 ml samples were withdrawn from the serosal compartment and the volume was replaced with fresh buffer.

After incubation with bovine serum albumin (BSA) complexes, monolayers were rigorously washed three times with HBSS, fixed with Formalin-HBSS (4%) for 30 min, embedded in glycerol gelatin, and imaged by confocal laser scanning microscopy (CLSM) for bioadhesion. The CLSM equipment consisted of a Zeiss Axiovert 100 microscope with Zeiss Neofluar 40×, 63×NA 1.3 oil objectives, a confocal laser scanning imaging system, and a helium Neon laser. The laser/filter settings (Exc/Emm) were BP 488/LP 515–525.

Cells after HSA-complex exposition were washed 3 times with buffer, fixed in 3% paraformaldehyde/0.1% glutaraldehyde in PBS (pH 7.4) for 2 hours at room temperature, and embedded in Lowicryl K4M (Piano, Wetzlar, Germany). Ultrathin sections were immunolabeled using polyclonal rabbit anti-human albumin antibodies, rinsed rigorously and incubated with an anti-rabbit-IgG, conjugated with 15 nm gold particles. After repeating the washing steps, samples were contrasted with uranyl acetate as well as lead citrate and examined with a Zeiss EM 10 electron microscope.

The integrity of the cell monolayer was determined at the beginning and at the end of all experiments by measuring the transepithelial electrical resistance (TEER) using an Endohm (WPI, Germany).

Identical experiments were performed with pure protein solutions (50 µg/ml) as negative control. For CLSM imaging the polymer complex counterpart was a fluorescently labeled BSA (FITC-BSA). As can be seen on the CLSM images, a major increase in cell-associated protein amount was found compared to the control experiment, where no protein could be localized on or in the cells. Similar results were obtained using inclusion-like complexes consisting of an uncharged polymer and human serum albumin (HSA), prepared by LCST precipitation at 37° C. TEM investigations revealed that small protein amounts were located at the cell surfaces. It is worth noting, that the incubation had no negative effect on the caco-2 cell monolayer, the transepithelial electrical resistance (TEER) did not change during these experiments.

EXAMPLE 4

The purpose of this example was to determine the oral performance of the complexes of the invention in mice using tetanus toxoid (Ttx) as a model antigen.

Animal studies were preformed according to Fischer et al., "A Novel Non-viral Vector for DNA Delivery Based on Low Molecular Weight, Branched Polyethylenimine: Effect of Molecular Weight on Transfection Efficiency and Cytotoxicity," *Pharm. Res.*, 16(8):1273–9 (1999). Female Balb/c mice, 7–9 weeks of age, weighing 16–22 g, were obtained from Harlan-Winkelmann (Germany). Three groups of mice were used in this experiment. Complex dispersions were compared to conventional alum-adsorbed as well as to free tetanus toxoid (Ttx).

Mice were randomized, pooled into groups of 10 animals, and immunized on three consecutive weeks (day 1, 8, and 15) by peroral (p.o.) application of 200 µl5 LF Ttx containing colloidal polyelectrolyte complexes. Inoculations via i.p. with 200 µl of Tetanol® were performed as a positive control. Animals were bled at week 0 and 4.

It is worth noting that the pH value of the stomach was not buffered in the in vivo experiments leaving gastric enzymes active. As can be seen in FIGS. 18 and 19, a significant increase of serum IgA and IgG titers could be achieved.

All sera were assayed in duplicate for Ttx specific IgG and IgA antibody responses using an ELISA technique. Serial dilutions of sera were incubated on TTF 6 coated microtiter plate wells. Ttx specific antibodies were quantitated by incubating wells with heavy chain-specific peroxidase conjugated goat anti mouse IgG or IgA. Responses were quantitated by measurement of optical densities (OD) at 450 nm following incubation of wells with TMB. The results were expressed as reciprocal end-point sera titers representing the highest sera dilutions giving OD values of 0.2.

While no substantial titers were observable after oral administration of a Ttx solution (even under stomach buffering conditions), the well-documented increase especially of IgG after intraperitoneal application of alum adsorbed Ttx (Tetanol) was found. An about 4 to 6 times higher IgA titer was achieved with the colloids compared to Tetanol, indicating their increased mucosal activity in vaccination. These results demonstrate the usefulness of colloidal vaccination with this novel polymeric carrier system.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A polyol ester comprising:

(a) a linear polyol containing greater than six hydroxyl groups as a central backbone;

(b) biodegradable hydroxy carboxylic ester groups attached to the central backbone, (c) wherein the linear polyol contains charged groups, proton donating groups, and/or proton accepting groups, which are attached via a spacer group or an ether-, ester- or urethane-linkage to the linear polyol, and (d) wherein the polyol ester has a lower critical solution temperature (LCST) in aqueous solution of between 0 and 100° C.

2. The polyol ester of claim 1, wherein the spacer group is an aliphatic group.

3. The polyol ester of claim 1, wherein the polyol backbone is selected from the group consisting of linear synthetic polymers having greater than about 6 and less than or equal to about 500 hydroxyl groups.

4. The polyol ester of claim 3, in which the polyol backbone is selected from the group consisting of polyvinyl alcohols having polymerization degrees of more than 6 and up to 500.

5. The polyol ester of claim 1, wherein the polyol backbone is a linear synthetic vinylcopolymer.

6. The polyol ester of claim 5, wherein the linear synthetic vinylcopolymer is a polyvinyl alcohol having polymerization degrees of more than about 6 and up to about 500.

7. The polyol ester of claim 5, wherein the linear synthetic vinylcopolymer comprises a vinylpyrrolidone, vinylamine, vinylimidazole, vinylpyridine, vinyl sulfonic acid, or vinyl phosphonic acid.

8. The polyol ester of claim 1, wherein the charged groups, proton donating groups, and/or proton accepting groups are attached via a spacer group to the backbone and are selected from the group consisting of carboxylic acid groups, sulfonic acid groups, sulfate groups, primary quaternary amino groups, secondary quaternary amino groups, tertiary quaternary amino groups, and quaternary amino groups.

9. The polyol ester of claim 8, wherein the groups connected via a spacer group to the backbone contain one or more substituents selected from the group consisting of carboxylic groups, sulfobutyl groups, and sulfopropyl groups.

10. The polyol ester of claim 8, wherein the groups connected via a spacer group to the backbone contain one or more substituents selected from the group consisting of butylamino-, propylamino- and ethylamino groups as primary, secondary, tertiary, or quaternary amino groups, wherein N-substituents can contain hydrogen or alkyl groups.

11. The polyol ester of claim 10, wherein the alkyl group is selected from the group consisting of methyl and ethyl groups.

12. The polyol ester of claim 1, wherein the biodegradable hydroxy carboxylic acid groups are derived from one or more of l-lactic acid, d-lactic acid, ϵ-caprolactone, and glycolic acid.

13. The polyol ester of claim 12, wherein the biodegradable hydroxy carboxylic acid groups are derived from dimers of one or more of l-lactic acid; d-lactic acid; d,l-lactic acid; and glycolic acid in any molar composition.

14. The polyol ester of claim 1, wherein the introduction of the biodegradable hydroxy carboxylic acid groups into the molecule retains the water-solubility of the central backbone.

15. The polyol ester of claim 1, characterized by a lower critical solution temperature (LCST) in aqueous solution in the temperature range between about 0 and about 100° C.

16. The polyol ester of claim 1, wherein the molar proportion of polyol hydroxyl groups and hydroxy carboxylic acid units are in the range of between about 0.6:1 and about 6:1.

17. The polyol ester of claim 16, wherein the molar proportion of polyol hydroxyl groups and hydroxy carboxylic acid units are in the range of between about 1:1 and about 3:1.

18. A polyol ester according to claim 1, wherein the hydroxy carboxylic add groups connected to the central backbone are each composed of about 1 to about 100 hydroxy carboxylic acid units.

19. A polyol ester according to claim 18, wherein the hydroxy carboxylic add groups connected to the central backbone are each composed of about 5 to about 50 hydroxy carboxylic acid units.

20. A complex in the form of a particle comprising a polyol ester according to claim 1 and an active ingredient.

21. The complex of claim 20, wherein the active ingredient is a water-soluble molecule possessing pharmacological activity.

22. The complex of claim 21, wherein the active ingredient is selected from the group consisting of peptides, proteins, enzymes, enzyme inhibitors, antigens, cytostatic agents, antiinflammatoric agents, antibiotics, DNA-constructs, RNA-constructs, and growth factors.

23. The complex of claim 21, wherein the particles possess a mean particle diameter of less than about 10 μm.

24. The complex of claim 23, wherein the mean particle diameter is less than about 1 μm.

25. The complex of claim 20 adapted for mucosal vaccination, wherein the active ingredient is selected from the group consisting of a peptide, a protein, RNA, and DNA.

26. A process for the manufacture of the complex of claim 20 comprising the steps:

(a) providing an aqueous solution of the polyol ester of claim 1, (b) increasing the temperature until a spontaneous in-situ formation of particles of polyol ester is formed.

27. The process of claim 26, wherein the aqueous solution of polyol ester additionally comprises an active ingredient, and when the temperature is increased in step (b), particles of polyol ester/active ingredient complex are formed.

28. The process of claim 26, additionally comprising contacting the polyol ester particles formed in step (b) with an active ingredient to form particles of polyol ester/active ingredient complex.

29. The process of claim 26, wherein the temperature after step (b) is increased above a lower critical solution temperature (LCST), which is in the range of between about 0 and about 100° C.

30. The process of claim 26, wherein after step (a), providing an aqueous solution of the polyol ester of claim 1, (a') a drug molecule is added which comprises a substituent selected from the group consisting of ionic groups, proton accepting groups, and proton donating groups, wherein the drug molecule substituents are capable of forming complexes with one or more of the ionic groups, proton accepting groups, and proton donating groups of the polyol ester to form particles of a polyol ester/drug molecule complex, and after step (b), forming the polyol ester/drug molecule complex particles, (c) adding additional drug molecules which are adsorbed by non-ionic interaction by the particles.

31. A method of mucosal delivery of an active ingredient to an organism comprising orally administering to the organism a formulation comprising the complex of claim 20.

32. A method of delivery of an active ingredient to an organism comprising administering to the organism a pulmonary and/or nasal formulation comprising the complex of claim 20.

* * * * *